US012286512B2

(12) United States Patent
Potkay et al.

(10) Patent No.: US 12,286,512 B2
(45) Date of Patent: Apr. 29, 2025

(54) PHOTOCURABLE RESIN FOR HIGH-RESOLUTION 3-D PRINTING

(71) Applicant: The United States Government as Represented by the Department of Veterans Affairs, Washington, DC (US)

(72) Inventors: Joseph Potkay, Ann Arbor, MI (US); Elyse Fleck, Ann Arbor, MI (US)

(73) Assignees: THE UNITED STATES GOVERNMENT AS REPRESENTED BY THE DEPARTMENT OF VETERANS AFFAIRS, Washington, DC (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 430 days.

(21) Appl. No.: 17/332,655

(22) Filed: May 27, 2021

(65) Prior Publication Data
US 2021/0371597 A1 Dec. 2, 2021

Related U.S. Application Data

(60) Provisional application No. 63/057,166, filed on Jul. 27, 2020, provisional application No. 63/030,848, filed on May 27, 2020.

(51) Int. Cl.
| | | |
|---|---|---|
| *C08L 83/04* | (2006.01) | |
| *A61M 1/16* | (2006.01) | |
| *B33Y 70/00* | (2020.01) | |
| *B33Y 80/00* | (2015.01) | |
| *C08G 77/18* | (2006.01) | |
| *C12M 1/04* | (2006.01) | |
| *C12M 3/06* | (2006.01) | |
| *G03F 7/00* | (2006.01) | |
| *G09B 23/30* | (2006.01) | |
| *B33Y 10/00* | (2015.01) | |
| *C08F 230/08* | (2006.01) | |

(52) U.S. Cl.
CPC ........... *C08G 77/18* (2013.01); *A61M 1/1698* (2013.01); *B33Y 70/00* (2014.12); *B33Y 80/00* (2014.12); *C12M 23/16* (2013.01); *C12M 23/24* (2013.01); *G03F 7/0037* (2013.01); *G09B 23/303* (2013.01); *B33Y 10/00* (2014.12); *C08F 230/08* (2013.01); *C08L 83/04* (2013.01)

(58) Field of Classification Search
CPC .............................. C08L 83/04; C08F 230/08
USPC ....................................................... 526/279
See application file for complete search history.

(56) References Cited

U.S. PATENT DOCUMENTS

| | | |
|---|---|---|
| 8,263,720 B1 | 9/2012 | Salamone et al. |
| 2011/0171480 A1 | 7/2011 | Mori et al. |
| 2015/0146159 A1 | 5/2015 | Archer et al. |
| 2016/0030362 A1 | 2/2016 | Liao et al. |
| 2016/0083602 A1* | 3/2016 | Secord ................... B41J 2/1721 347/77 |
| 2018/0273657 A1* | 9/2018 | Wang ........................ C08F 2/48 |
| 2020/0071525 A1* | 3/2020 | Folch .................... G03F 7/0757 |

FOREIGN PATENT DOCUMENTS

| | | | |
|---|---|---|---|
| WO | 2018/058136 | * | 3/2018 |
| WO | 2019/067604 A1 | | 4/2019 |

OTHER PUBLICATIONS

Bhattacharjee, N. et al. (2018), Advanced Materials, 30(22), 1800001.
Bhattacharjee, N. et al. (2018), Advanced Materials, 30(22), 1800001, Supporting Information.
Dabaghi, M., et al. (2018). Lab on a Chip, 18(24), 3780-3789.
Femmer, T., Kuehne, A. J., & Wessling, M. (2014). Lab on a Chip, 14(15), 2610-2613.
Gökaltun, A., Kang, Y.B.(., Yarmush, M.L et al. Sci Rep 9, 7377 (2019), 41598-019-43625-5.
Gong, H. et al. (2017), Lab on a Chip 17(17), 2899-2909.
Gong, H., et.al. (2015). RSC advances,5(129), 106621-106632.
Hoganson, D. M., et al. (2011). Lab on a Chip, 11(4), 700-707.
Kaner et al., Journal of Membrane Science 2017, vol. 533, pp. 141-159.
Kniazeva, T., et al. (2011). Biomedical microdevices, 13(2), 315-323.
Kuo, A. P. et al. (2019), Advanced Materials Technologies, 4(6), 1, 800395.
Macdonald, N. P., et al. (2017). Analytical chemistry, 89(7), 3858-3866.
Matharoo, H., et al. (2018). Biomicrofluidics, 12(1), 014107.
Münch, A. S., Adam, S., Fritzsche, T., Uhlmann, P., Adv. Mater. Interfaces 2020, 7, 1901422.
Potkay, J. A., et al. (2011). Lab on a Chip, 11(17), 2901-2909.
Thompson, A. J., et al. (2017). Biomicrofluidics, 11(2), 024113.
Thompson. A., et al. (2018). IEEE Transactions on Biomedical Engineering, 66(4), 1082-1093.
Urrios, A. et al., Lab Chip, 2016, 16, 2287.
Yao, M; Fang, J. 2012 J. Micromech. Microeng. 22 025012.

(Continued)

*Primary Examiner* — Margaret G Moore
(74) *Attorney, Agent, or Firm* — Ballard Spahr LLP

(57) ABSTRACT

Provided are photocurable resins comprising a poly(siloxane)-based copolymer together with a photoinitiator, and other optional ingredients such as a photocurable diluent, a photoabsorber, a photosensitizer, or a hydrophillic additive. Also provided are methods of stereolithographically printing a 3-D object from a disclosed resin. Also provided is an improved method for stereolithographically printing a 3-D object, the improvement comprising the use of a disclosed photocurable resin. Further provided is a 3-D microfluidic device such as an artificial lung prepared from a disclosed photocurable resin.

18 Claims, 13 Drawing Sheets

(56) References Cited

OTHER PUBLICATIONS

Fleck, Elyse et al. "Advancing 3D-Printed Microfluidics: Characterization of a Gas-Permable, High-Resolution PDMS Resin for Stereolithography", Micromachines, 2021, 12, 1266, pp. 1-14.

Fleck, Elyse et al. "Low-Viscosity Polydimethlsiloxane Resin for Facile 3D Printing of Elastomeric Microfluidics", Micromachines, 2023, 14, 773, pp. 1-16.

* cited by examiner

PHOTOCURABLE RESIN FOR HIGH-RESOLUTION 3-D PRINTING

CROSS-REFERENCE TO RELATED APPLICATIONS

This application claims priority to U.S. Provisional Application No. 63/030,848, filed May 27, 2020, and U.S. Provisional Application No. 63/057,166, filed Jul. 27, 2020, both of which are incorporated by reference in their entirety.

GOVERNMENT SUPPORT

This invention was made with government support under grant no. HL144660, awarded by the National Institutes of Health. The government has certain rights in the invention.

BACKGROUND

The field of 3-D printing has seen significant advancement in the last decade, particularly with respect to resolution capabilities and material development. Until recently, 3-D printing was limited to early design stage prototyping but is now being used as a legitimate manufacturing practice to deliver end performance devices. Substantial research has focused on the area of industrial-grade and high performing engineering materials. From dental aligners to shoes, the expansion of the 3-D printing industry has proven valuable in nearly every market.

Microfluidics has been one of the last markets to receive adequate attention in the 3-D printing industry. Current fabrication techniques of microfluidics require slow, manual steps and restrict device designs to 2-D, driving a need for automation and scalability. While the resolution capabilities of 3-D printers have met certain requirements of the microfluidics market, material development remains insufficient. Gas permeable materials (e.g., polydimethylsiloxane or PDMS) are commonplace in microfluidics, but the use of these materials in 3-D printing applications is currently absent. Presently, there are no commercially sold resins available with adequate gas permeability and high-resolution printing capabilities. This need and others are met by the following photocurable resins.

SUMMARY

In one aspect, disclosed is a photocurable resin comprising: (a) 5-99% by weight of a copolymer having a methacryloxypropyl-methysiloxane repeating unit represented by formula (I):

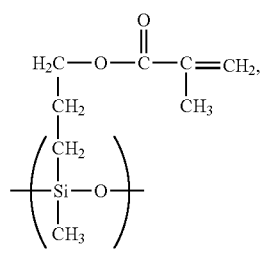

and a dimethylsiloxane repeating unit represented by formula (II):

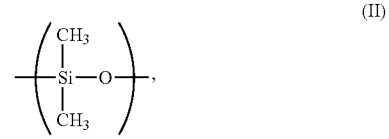

wherein the methacryloxypropyl-methysiloxane repeating unit constitutes 1-10 mol % of the copolymer, and the dimethylsiloxane repeating unit constitutes the balance of the mol % of the copolymer, and wherein the copolymer has a viscosity average molecular weight ($M_v$) ranging from about 20 kDa to about 60 kDa; (b) 10-95% by weight of a methacryloxypropyl terminated dimethylsiloxane represented by formula (IV):

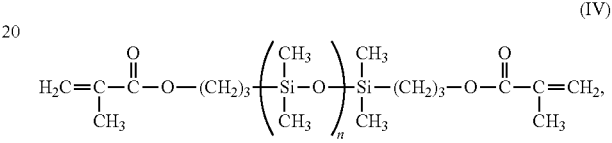

wherein n is an integer ranging from 1 to 350; and (c) 0.01-10% by weight of a phosphine oxide photoinitiator selected from phenylbis(2,4,6-trimethylbenzoyl)phosphine oxide, diphenyl-(2,4,6, trimethylbenzoyl)phosphine oxide (TPO), ethyl (2,4,6-trimethylbenzoyl)phenylphosphinate (TPO-L), or a combination thereof.

In a further aspect, disclosed herein is a method for stereolithographically printing a 3-D object, comprising providing a disclosed photocurable resin, selectively photopolymerizing a first portion of the resin to provide a first photocured layer, and selectively photopolymerizing a second portion of the resin to provide a second photocured layer, wherein the first and second photocured layers form an integral photocured layer.

In a still further aspect, disclosed herein is an improved method for stereolithographically printing a 3-D object, the improvement comprising the use of a disclosed photocurable resin.

In yet a further aspect, disclosed herein is a 3-D microfluidic device, e.g., an artificial lung, printed from a disclosed photocurable resin.

Still other objects and advantages of the present disclosure will become readily apparent by those skilled in the art from the following detailed description, which is shown and described by reference to preferred aspects, simply by way of illustration of the best mode. As will be realized, the disclosure is capable of other and different aspects, and its several details are capable of modifications in various respects, without departing from the disclosure. Accordingly, the description is to be regarded as illustrative in nature and not as restrictive.

BRIEF DESCRIPTION OF THE DRAWINGS

The accompanying drawings, which are incorporated in and constitute a part of this specification and together with the description, serve to explain the principles of the disclosed photocurable resins and methods.

As shown in FIG. 4B, channels identified in FIG. 4A were successfully cleared of uncured polymer exposing 58±3 μm channels.

As shown in FIG. 4C, these channels had membranes as thin as 20 μm.

DETAILED DESCRIPTION

Figure 1:
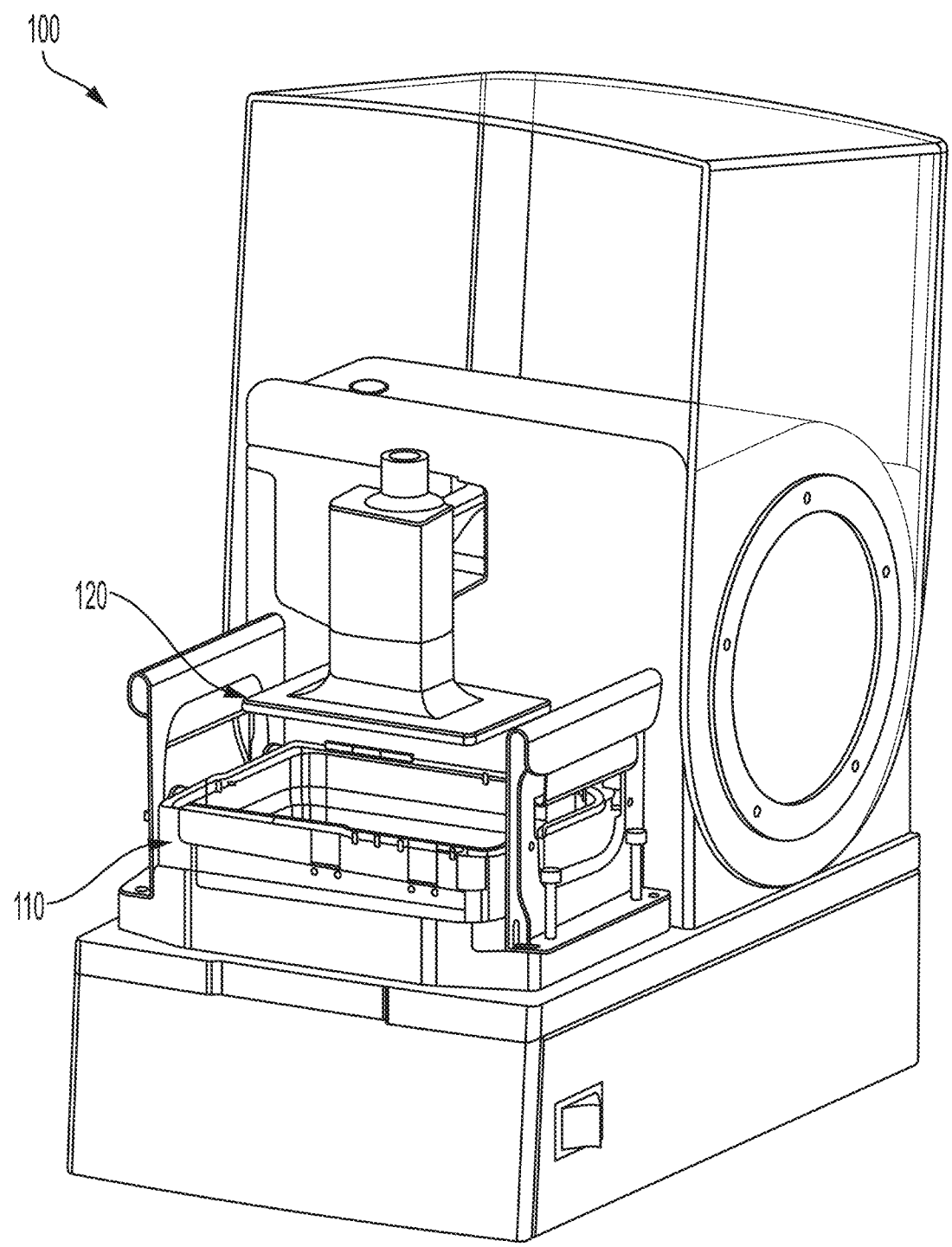
FIG. 1 depicts a stereolithographic (SLA-DLP) 3-D Printer.

The present invention can be understood more readily by reference to the following detailed description of the invention and the Examples included therein.

Disclosed are components that can be used to perform the disclosed methods. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and products. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

While aspects of this disclosure can be described and claimed in a particular statutory class, this is for convenience only and one of skill in the art will understand that each aspect of this disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present application is not entitled to antedate such publication by virtue of prior invention. Further, stated publication dates may be different from actual publication dates, which can require independent confirmation.

A. Definitions

Listed below are definitions of various terms. These definitions apply to the terms as they are used throughout this specification, unless otherwise limited in specific instances, either individually or as part of a larger group.

As used in the specification and in the claims, the term "comprising" can include the aspects "consisting of" and "consisting essentially of."

As used in the specification and claims, the singular forms "a," "an," and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

"Optional" or "optionally" means that the subsequently described event or circumstance may or may not occur, and that the description includes instances where said event or circumstance occurs and instances where it does not.

As used herein, the term "by weight," when used in conjunction with a component, unless specially stated to the contrary is based on the total weight of the formulation or composition in which the component is included. For example, if a particular element or component in a composition or article is said to have 8% by weight, it is understood that this percentage is in relation to a total compositional percentage of 100%. A weight percent of a component, or weight %, or wt %, unless specifically stated to the contrary, is based on the total weight of the formulation or composition in which the component is included.

References in the specification and concluding claims to parts by weight of a particular element or component in a composition or product, denotes the weight relationship between the element or component and any other elements or components in the composition or product for which a part by weight is expressed. Thus, in a composition or a selected portion of a composition containing 2 parts by weight of component X and 5 parts by weight component Y, X and Y are present at a weight ratio of 2:5, and are present in such ratio regardless of whether additional components are contained in the composition.

As used herein, the term "substantially," in, for example, the context "substantially free of" refers to a composition having less than about 10% by weight, e.g., less than about 5%, less than about 1%, less than about 0.5%, less than about 0.1%, less than about 0.05%, or less than about 0.01% by weight of the stated material, based on the total weight of the composition.

It is further understood that the term "substantially," when used in reference to a composition, refers to at least about 60% by weight, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% by weight, based on the total weight of the composition, of a specified feature, component, or a combination of the components. It is further understood that if the composition comprises more than one component, the two or more components can be present in any ratio predetermined by one of ordinary skill in the art.

B. Photocurable Resin

In one aspect, this disclosure relates to a photocurable resin comprising a poly(siloxane)-based copolymer together with a photoinitiator, and other optional components such as a photoabsorber, a photosensitizer, a photocurable diluent, and/or a hydrophillic additive. The poly(siloxane)-based copolymer includes a side-chain methacrylate functional group that enables the copolymer to be cured when exposed to UV light. The photocurable resin is useful for, among other things, 3-D printing applications which benefit from small feature sizes, including without limitation, microfluidics.

1. Photocurable Copolymer

In one aspect, the photocurable polymer is a poly(siloxane) copolymer comprising a photocurable, methacryloxypropyl-methysiloxane repeating unit represented by formula (I):

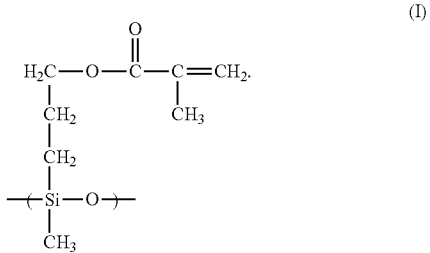

The side-chain methacrylate functional group of the photocurable repeating unit represented by formula (I) can be reactive toward free-radical polymerization initiated by UV light, and thus capable of curing the resin. In one aspect, the photocurable copolymer can comprise from about 1% to about 10% by mol of the methacryloxypropyl-methysiloxane repeating unit represented by formula (I). In a further aspect, the methacryloxypropyl-methysiloxane repeating unit represented by formula (I) constitutes from about 7% to about 9% by mol of the copolymer.

In various aspects, a dimethylsiloxane repeating unit represented by formula (II) constitutes the balance of the mol % of the copolymer.

Thus, the photocurable copolymer can comprise from about 90% to about 99% by mol of the dimethylsiloxane repeating unit represented by formula (II). In one aspect, the photocurable copolymer can comprise from about 91% to about 93% by mol of the dimethylsiloxane repeating unit represented by formula (II).

Together, the two repeating units of the photocurable polymer are represented by formula (III):

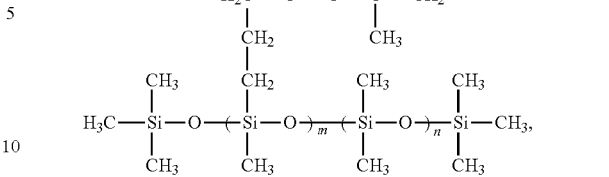

where m and n are independent integers greater than two. Integers m and n can vary depending on the molecular weight of the photocurable polymer. In one aspect, the photocurable polymer has a viscosity average molecular weight ($M_v$) ranging from about 20 kDa to about 60 kDa. In a further aspect, the photocurable polymer comprising from about 2% to about 4% by mol of the methacryloxypropyl-methysiloxane repeating unit represented by formula (I) has a viscosity average molecular weight ($M_v$) of about 25 kDa. In another aspect, the photocurable polymer comprising from about 4% to about 6% by mol of the methacryloxypropyl-methysiloxane repeating unit represented by formula (I) has a viscosity average molecular weight ($M_v$) of about 57 kDa. In a still further aspect, the photocurable polymer comprising from about 7% to about 9% by mol of the methacryloxypropyl-methysiloxane repeating unit represented by formula (I) has a viscosity average molecular weight ($M_v$) of about 38 kDa.

Molecular weight of the photocurable polymer can be measured using methods known in the art. Viscosity average molecular weights ($M_v$) can be defined by the following equation:

$$M_v = \left[\sum w_x M_x^a\right] \wedge 1/a = \left[\frac{\Sigma N_x M_x^{a+1}}{\Sigma N_x M_x}\right] \wedge 1/a$$

where a is a constant. Viscosity and weight average molecular weights are equal when a is unity. $M_v$ is often less than weight average molecular weight ($M_w$), since a is often in the range 0.5-0.9. However, $M_v$ can be closer to $M_w$ than number average molecular weight ($M_n$), usually within 20% of $M_w$. The value of a can depend on the hydrodynamic volume of the polymer, the effective volume of the solvated polymer molecule in solution, and varies with polymer, solvent, and temperature, as one of ordinary skill in the art will appreciate.

In general, the resin can comprise from about 5-99% by weight of the copolymer represented by formula (III). In some aspects, when the methacryloxypropyl terminated dimethylsiloxane diluent is not present in the resin formulation, the resin can comprise from about 80-99% by weight of the copolymer represented by formula (III), e.g., 85-99%, 90-99%, or 95-99%. In other aspects, when the methacryloxypropyl terminated dimethylsiloxane diluent is present in the resin formulation, the resin can comprise from about 5-50% by weight of the copolymer represented by formula (III), e.g., from about 8-40%.

In various aspects, the photocurable polymer can be prepared according to methods known in the art. Common methods for making poly(dimethylsiloxane) polymers utilize a dimethyldichlorosilane monomer and water, which provides a polymer having silanol end groups that are typically capped by reacting with trimethylsilyl chloride to provide trimethylsilane end groups such as those represented in formula (III). The methacryloxypropyl-methysiloxane repeating unit can be prepared by polymerizing a suitable silane precursor. The polymerization of each repeating unit can occur in tandem, e.g., to provide a random copolymer, or can proceed in sequence to produce a block copolymer or copolymer with another architecture. In other aspects, the photocurable polymer can be obtained commercially. In one aspect, for example, the photocurable polymer is a commercially-available copolymer having about 7% to about 9% by mol of the methacryloxypropyl-methysiloxane repeating unit, with the dimethylsiloxane repeating unit constituting the balance of the mol % (e.g., Product Code RMS-083, CAS No. 104780-61-2, available from Gelest, Inc., Morrisville, Pa.).

2. Methacryloxypropyl Terminated Dimethylsiloxane Diluent

In various aspects, the photocurable resin comprises 10-95% by weight of a methacryloxypropyl terminated dimethylsiloxane represented by formula (IV):

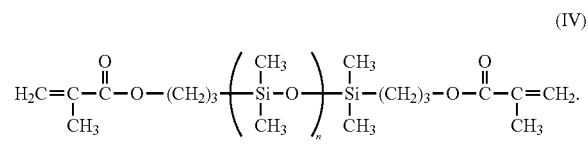

(IV)

The methacryloxypropyl terminated dimethylsiloxane represented by formula (IV) can in some aspects be useful to reduce the viscosity of a solution comprising the photocurable copolymer represented by formula (III), thereby permitting the photocurable resin to be useful in a variety of 3-D printing applications.

The methacryloxypropyl terminated dimethylsiloxane represented by formula (IV) can in some aspects be photocured along with the copolymer represented by formula (III) when the photoinitiator initiates photopolymerization of the methacrylate functional groups on the polymers represented by formula (III) and formula (IV).

In some aspects, the methacryloxypropyl terminated dimethylsiloxane represented by formula (IV) can be a monomer having a molecular weight of about 386 g/mol. In other aspects, the polymer can be a methacryloxypropyl terminated polydimethylsiloxane having a higher molecular weight generally up to 25,000 g/mol. Thus, n in formula (IV) can correspond to an integer ranging from 1 to 350, representing a molecular weight range of about 386 g/mol to about 25,000 g/mol. Integer n in formula (IV) can be any suitable integer corresponding to a molecular weight from about 386 g/mol to about 25,000 g/mol. For example, n can be an integer ranging from about 60-65 (corresponding to a molecular weight of about 5,000 g/mol), 120-135 (corresponding to a molecular weight of about 10,000 g/mol), or 325-335 (corresponding to a molecular weight of about 25,000 g/mol).

In one exemplary aspect, the methacryloxypropyl terminated dimethylsiloxane represented by formula (IV) can be a commercially-available polymer having a molecular weight of about 10,000 g/mol (e.g., Product Code DMS-R22, CAS No. 58130-03-3, available from Gelest, Inc., Morrisville, Pennsylvania).

The weight % of the methacryloxypropyl terminated dimethylsiloxane represented by formula (IV) can vary depending on the desired viscosity of the resin and the particular 3-D printing application. In some aspects, the photocurable resin comprises 10-95% by weight of the methacryloxypropyl terminated dimethylsiloxane represented by formula (IV). In other aspects, the photocurable resin comprises 20-95% by weight of the methacryloxypropyl terminated dimethylsiloxane represented by formula (IV). In further aspects, the photocurable resin comprises 30-95% by weight of the methacryloxypropyl terminated dimethylsiloxane represented by formula (IV). In still further aspects, the photocurable resin comprises 50-95% by weight of the methacryloxypropyl terminated dimethylsiloxane represented by formula (IV). In additional aspects, the photocurable resin comprises 70-95% by weight of the methacryloxypropyl terminated dimethylsiloxane represented by formula (IV). In further aspects, the photocurable resin comprises 70-90% by weight of the methacryloxypropyl terminated dimethylsiloxane represented by formula (IV). For example, the photocurable resin can comprise about 70%, 75%, 80%, 85%, or 90% by weight of the methacryloxypropyl terminated dimethylsiloxane represented by formula (IV).

In some aspects, the amount of methacryloxypropyl terminated dimethylsiloxane diluent can be combined with a suitable amount of the photocurable copolymer represented by Formula (III) based on the flow characteristics of a resin prepared from the combination of polymers. In some aspects, for example, methacryloxypropyl terminated dimethylsiloxane diluents can provide for non-flowable resins when they comprises greater than 5 mol % methacrylate substitution. Thus, for example, in some aspects, a photocurable copolymer such as [7-9% (Methacryloxypropyl) methylsiloxane]-dimethylsiloxane copolymer (RMS-083, Gelest) can be combined with a commercially-available polymer having a molecular weight of about 10,000 g/mol (e.g., Product Code DMS-R22, Gelest) in a resin with up to 90% by weight of DMS-R22 to provide a non-flowable cross-linked resin. Similarly, in other aspects, a photocurable copolymer such as [2-4% (Methacryloxypropyl)methylsiloxane]-dimethylsiloxane copolymer (RMS-033, Gelest) can be combined with a commercially-available polymer having a molecular weight of about 10,000 g/mol (e.g., DMS-R22, Gelest) with up to 70% by weight of DMS-R22 to provide a non-flowable cross-linked resin.

In a further aspect, a photocurable copolymer such as RMS-033, RMS-083, or RMS-044 (all commercially-available from Gelest) can be combined with other suitable methacryloxypropyl terminated dimethylsiloxane diluents including without limitation commercially-available polymers such as DMS-R05 (380-550 g/mol, Gelest), DMS-R11 (900-1,200 g/mol, Gelest), DMS-R18 (4,500-5,500 g/mol, Gelest), DMS-R22 (Gelest), DMS-R31 (25,000 g/mol, Gelest), or a combination thereof.

3. Photoinitiator

In various aspects, the photocurable resin comprises a photoinitiator. Without wishing to be bound by theory, when printing a 3-D object using a disclosed resin, the photoinitiator absorbs light from the UV-light source used for photocuring and/or absorbs energy from the photosensitizer described below to initiate photopolymerization of the side-chain methacrylate functional group of the photocurable repeating unit represented by formula (I) and the methacrylate functional group of the diluent represented by formula (IV).

In general, the photoinitiator can be selected based on the wavelength of the light source used for photocuring. The resin described herein is suitable for use with a variety of 3-D printing technologies, including for example digital light processing (DLP) stereolithography printers, which are typically available with 385 nm or 405 nm UV light sources. Thus, in some aspects, the photoinitiator has a light absorbance that overlaps with the wavelength from the light source of a stereolithography 3-D printer. Additionally, in some aspects, the photoinitiator can be selected based both on its UV-absorbance profile and its solubility in the copolymer present in the photocurable resin.

Thus, in some aspects, the photoinitiator has a light absorbance in the range of from about 375 nm to about 425 nm. Suitable photoinitiators include without limitation Type I photoinitiators, which when exposed to UV light undergo a cleavage reaction into two radical fragments. In one aspect, the photoinitiator is a phosphine oxide photoinitiator. Non-limiting examples of phosphine oxide photoinitiators include Phenylbis(2,4,6-trimethylbenzoyl)phosphine oxide, Diphenyl-(2,4,6, Trimethylbenzoyl)phosphine oxide (TPO), Ethyl (2,4,6-trimethylbenzoyl)phenylphosphinate (TPO-L), represented by the following formulae, or a combination thereof.

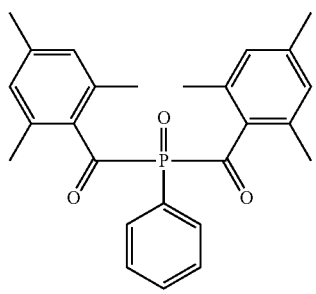

Phenylbis(2,4,6-trimethylbenzoyl)phosphine oxide

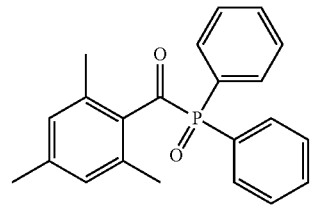

TPO

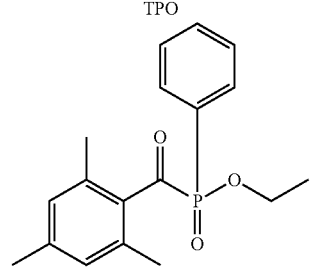

TPO-L

In one aspect, the photoinitiator is TPO-L. TPO-L is less reactive than TPO, for example, and is a liquid at room temperature, facilitating easier incorporation of TPO-L into a disclosed resin. TPO-L also exhibits good solubility in the disclosed resins.

In other aspects, the photoinitiator can be an acylphospine oxide. Suitable examples include without limitation phosphine oxide-phenyl-bis-(2,4,6-trimethyl benzoyl) (e.g., IRGACURE 819), a liquid blend of acyl phosphine oxides (e.g., IRGACURE 2100), 2,4,6-trimethylbenzoyl-diphenylphosphine oxide (e.g., LUCIRIN TPO), or a combination thereof, such as for example a combination of IRGACURE 819 (20 wt % relative to the total weight of the photoinitiator) with DAROCURE 1173 (80 wt % relative to the total weight of the photoinitiator). In a further aspect, the photoinitiator can be a benzoin ether derivative such as ethyl benzoin.

In various aspects, the photoinitiator is present in a disclosed resin in an amount ranging from about 0.01% to about 10% by weight, relative to the total weight of the resin. In one aspect, the photoinitiator is present in a disclosed resin in an amount ranging from about 0.1% to about 10% by weight. In a further aspect, the resin comprises from about 0.5% to about 1% by weight of the photoinitiator. In a still further aspect, the resin comprises about 0.8% by weight of the photoinitiator. In further aspects, the resin comprises from about 0.05% to about 10% by weight of TPO-L, e.g., from about 0.1% to about 1% by weight of TPO-L, from about 0.5% to about 1% by weight of TPO-L, or about 0.8% by weight of TPO-L.

4. Photoabsorber

In some aspects, the photocurable resin can comprise a photoabsorber. In general, suitable photoabsorbers are those that absorb UV light and assist in improving the resolution of 3-D printing, particularly resolution in on the Z-axis. Thus, in one aspect, the photoabsorber can have an absorbance in the range of about 300 nm to about 460 nm or higher. Suitable photoabsorbers include without limitation carbon black nanoparticles or microparticles and various azo dyes, such as for example 1-(Phenyldiazenyl)naphthalen-2-ol (Sudan I), 1-(2,4-Dimethylphenylazo)-2-naphthol (Sudan II), represented by the following formulae, or a combination thereof. In one aspect, the photoabsorber is 1-(Phenyldiazenyl)naphthalen-2-ol (Sudan I).

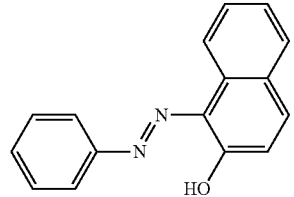

Sudan I

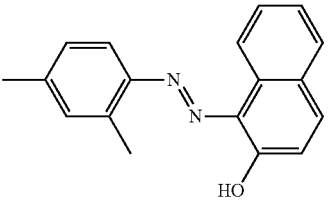

Sudan II

Other suitable photoabsorbers include without limitation morin hydrate (flavonoid), Coumarin 102 (dye), Curcumin (flavonoid), Quercetin (flavonoid), hydroxyphenyl-triazine (HPT) (e.g., TINUVIN 400), hydroxyphenyl-benzotriazole (e.g., TINUVIN 900), 2-nitrophenyl phenyl sulfide (NPS), or a combination thereof.

In various aspects, the photoabsorber is present in a disclosed resin in an amount ranging from about 0.01 to about 5% by weight, relative to the total weight of the resin. In a further aspect, the resin comprises from about 0.03% to about 1% by weight of the photoabsorber. In a further aspect, the resin comprises from about 0.04% to about 1% by weight of the photoabsorber. In a further aspect, the resin comprises from about 0.05% to about 1% by weight of the photoabsorber. In a further aspect, the resin comprises from about 0.05% to about 0.5% by weight of the photoabsorber. In a further aspect, the resin comprises from about 0.05% to about 0.2% by weight of the photoabsorber. In a further aspect, the resin comprises from about 0.05% to about 0.1% by weight of the photoabsorber.

In some exemplary aspects, the photoabsorber is present in a disclosed resin is Sudan I and is present in an amount ranging from about 0.01 to about 5% by weight, relative to the total weight of the resin. In a further aspect, the resin comprises from about 0.03% to about 1% by weight of Sudan I. In a further aspect, the resin comprises from about 0.04% to about 1% by weight of Sudan I. In a further aspect, the resin comprises from about 0.05% to about 1% by weight of Sudan I. In a further aspect, the resin comprises from about 0.05% to about 0.5% by weight of Sudan I. In a further aspect, the resin comprises from about 0.05% to about 0.2% by weight of Sudan I. In a further aspect, the resin comprises from about 0.05% to about 0.1% by weight of Sudan I. In one specific aspect, the resin comprises about 0.5% by weight of Sudan I.

5. Photosensitizer

In some aspects, the photocurable resin can comprise a photosensitizer. Suitable photosensitizers include without limitation thioxanthone compounds, such as for example, 2-chloro-thioxanthone isopropylthioxanthone (ITX), represented by the following formulae, or a combination thereof.

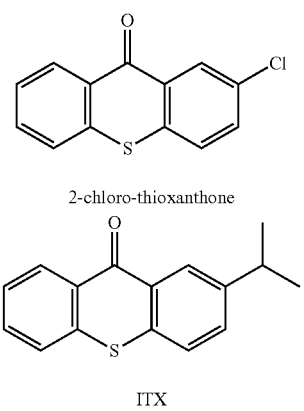

2-chloro-thioxanthone

ITX

In other aspects, suitable photosensitizers can include without limitation benzophenone, methyl phenylglyoxylate, iodonium salts, pyrromethene 567, N-phenylglycine, or a combination thereof.

In various aspects, the photocurable resin comprises the photosensitizer in an amount ranging from about 0.01% to about 5% by weight, relative to the total weight of the resin. In a further aspect, the resin comprises from about 0.01% to about 1% by weight of the photosensitizer. In a still further aspect, the resin comprises from about 0.3% to about 1% by weight of the photosensitizer. In yet a further aspect, the resin comprises about 0.4% by weight of the photosensitizer.

In further aspects, the resin comprises from about 0.01% to about 5% by weight of ITX. In a further aspect, the resin comprises from about 0.1% to about 1% by weight of ITX. In a still further aspect, the resin comprises from about 0.3% to about 1% by weight of ITX. In yet a further aspect, the resin comprises about 0.4% by weight of ITX.

6. Hydrophillic Additive

In some aspects, the photocurable resin can comprise a hydrophillic additive. Without wishing to be bound by theory, it is believed that the addition of the hydrophillic additive to the photocurable resin can in some aspects improve the wettability of the surface of a 3-D object printed from the resin. In general, wettability can be measured by water contact angles. If the water contact angle is smaller than 90°, the surface of the object is generally considered hydrophillic, whereas a water contact angle larger than 90° generally corresponds to a hydrophobic surface. For biomedical applications utilizing the disclosed resins, increased surface hydrophilicity can have several advantages, including a decrease of non-specific protein absorption while retaining biocompatability, in addition to exhibiting adequate mechanical properties.

In some aspects, the additive can be a hydrophilic molecule such as a poly-C1-C4 alkyl oxide (e.g., polyethylene glycol (PEG), also known as polyethylene oxide (PEO)) tethered to a hydrophobic chain such as polydimethylsiloxane (PDMS) (e.g., PEG-PDMS or PEO-PDMS) or to a photoactive group such as methacrylate. The hydrophilic molecule can also be a zwitterion such as a sulfur-containing zwitterion (e.g., a sulfobetaine), a carboxybetaine, a phosphorous-containing zwitterion (e.g., a phosphorylcholine), or another suitable betaine. "Betaine" refers to any zwitterionic compound with a positively charged cationic functional group (e.g., a quaternary ammonium or phosphonium cation) together with a negatively charged functional group such as a carboxylate, sulfonate, phosphonate, and the like.

In some aspects, suitable zwitterionic groups can be classified into sulfobetaine (SB), carboxybetaine (CB), phosphorylcholine (PC), according to anions. Specifically, a zwitterionic group is an SB when anions are sulfonates, a CB when anions are carboxylates, and a PC when anions are phosphonates.

Non-limiting examples of suitable hydrophillic additives include those listed in Table 1.

TABLE 1

EXEMPLARY HYDROPHILLIC ADDITIVES

| Name | Structure | Source |
|------|-----------|--------|
| Dimethylsiloxane-(60-70% ethylene oxide) block co-polymer | $H_3C-Si(CH_3)_2-O-(Si(CH_3)((CH_2)_3-O(CH_2CH_2O)_pCH_3)-O)_m-(Si(CH_3)_2-O)_n-Si(CH_3)_3$ | Gelest DBE-712 (CAS No. 27306-78-1) (Molecular weight 600 g/mol) |

TABLE 1-continued

EXEMPLARY HYDROPHILLIC ADDITIVES

| Name | Structure | Source |
|---|---|---|
| Dimethylsiloxane-(25-30% ethylene oxide) block co-polymer | (structure with $O(CH_2CH_2O)_pCH_3$ pendant group on siloxane backbone with $m$ and $n$ repeat units) | Gelest DBE-224 (CAS No. 68938-54-5) (Molecular weight 10,000 g/mol) |
| Dimethylsiloxane-(30-35% ethylene oxide) block co-polymer | (structure with $O(CH_2CH_2O)_pCH_3$ pendant group on siloxane backbone with $m$ and $n$ repeat units) | Gelest DBE-311 (CAS No. 68938-54-5) (Molecular weight 800-1,200 g/mol) |
| Dimethylsiloxane-(50-55% ethylene oxide) block co-polymer | (structure with $O(CH_2CH_2O)_pCH_3$ pendant group on siloxane backbone with $m$ and $n$ repeat units) | Gelest DBE-621 (CAS No. 68938-54-5) (Molecular weight 2,500 g/mol) |
| Dimethylsiloxane-(80% ethylene oxide) block co-polymer | (structure with $O(CH_2CH_2O)_pCH_3$ pendant group on siloxane backbone with $m$ and $n$ repeat units) | Gelest DBE-814 (CAS No. 117272-76-1) (Molecular weight 1,000 g/mol) |
| Dimethylsiloxane-(80-85% ethylene oxide) block co-polymer | (structure with $O(CH_2CH_2O)_pCH_3$ pendant group on siloxane backbone with $m$ and $n$ repeat units) | Gelest DBE-821 (CAS No. 68938-54-5) (Molecular weight 4,400 g/mol) |
| Dimethylsiloxane-(propylene oxide-ethylene oxide) block copolymer | (structure with $O(CH_2CH_2O)_p(CH_2CHO(CH_3))_qCH_3$ pendant group on siloxane backbone with $m$ and $n$ repeat units) | Gelest DPB-313 (CAS No. 68937-55-3) |
| Dimethylsiloxane-[50-55% (60% propylene oxide/40% ethylene oxide)] block copolymer | (structure with $O(CH_2CH_2O)_p(CH_2CHO(CH_3))_q$H pendant group on siloxane backbone with $m$ and $n$ repeat units) | Gelest DBP-534 (CAS No. 68937-55-3) (Molecular weight 30,000 g/mol) |
| N,N,N-trimethylglycine | (trimethylammonium acetate zwitterion structure) | Various |
| 2-(Methacryloyloxy)ethyl]dimethyl-(3-sulfopropyl)ammonium hydroxide | (methacrylate ester with dimethylammonium propylsulfonate zwitterion structure) | Sigma-Aldrich (CAS No. 3637-26-1) |

TABLE 1-continued

EXEMPLARY HYDROPHILLIC ADDITIVES

| Name | Structure | Source |
|---|---|---|
| 3-(Decyldimethylammonio)-propane-sulfonate inner salt | [structure] | Sigma-Aldrich (CAS No. 15163-36-7) |
| 3-[Dimethyl-(2-hydroxyethyl)ammonio]-1-propanesulfonate | [structure] | Sigma-Aldrich (CAS No. 38880-58-9) |
| 2-Methacryloyloxyethyl phosphorylcholine (MPC) | [structure] | Sigma-Aldrich (CAS No. 67881-98-5) |

In some aspects, the resin comprises from 0.01-20% by weight of the hydrophillic additive. In one aspect, the resin comprises from 0.01-10% by weight of the hydrophillic additive. In another aspect, the resin comprises from 0.01-5% by weight of the hydrophillic additive. In another aspect, the resin comprises from 0.01-3% by weight of the hydrophillic additive. In another aspect, the resin comprises from 0.1-2% by weight of the hydrophillic additive. In another aspect, the resin comprises from 0.5-2% by weight of the hydrophillic additive. In another aspect, the resin comprises from 0.8-2% by weight of the hydrophillic additive.

In a further aspect, the resin comprises from 0.01-20% by weight of Dimethylsiloxane-(60-70% ethylene oxide) block co-polymer. In one aspect, the resin comprises from 0.01-10% by weight of Dimethylsiloxane-(60-70% ethylene oxide) block co-polymer. In another aspect, the resin comprises from 0.01-5% by weight of Dimethylsiloxane-(60-70% ethylene oxide) block co-polymer. In another aspect, the resin comprises from 0.01-3% by weight of Dimethylsiloxane-(60-70% ethylene oxide) block co-polymer. In another aspect, the resin comprises from 0.1-2% by weight of Dimethylsiloxane-(60-70% ethylene oxide) block co-polymer. In another aspect, the resin comprises from 0.5-2% by weight of Dimethylsiloxane-(60-70% ethylene oxide) block co-polymer. In another aspect, the resin comprises from 0.8-2% by weight of Dimethylsiloxane-(60-70% ethylene oxide) block co-polymer.

In a further aspect, the resin comprises from 0.01-20% by weight of 2-Methacryloyloxyethyl phosphorylcholine (MPC). In one aspect, the resin comprises from 0.01-10% by weight of MPC. In another aspect, the resin comprises from 0.01-5% by weight of MPC. In another aspect, the resin comprises from 0.01-3% by weight of MPC. In another aspect, the resin comprises from 0.1-2% by weight of MPC. In another aspect, the resin comprises from 0.5-2% by weight of MPC. In another aspect, the resin comprises from 0.8-2% by weight of MPC.

Specific, non-limiting examples of the photocurable resin (with and without the methacyloxypropyl terminated dimethylsiloxane diluent) include those listed in Table 2 and Table 3.

TABLE 2

EXEMPLARY RESIN FORMULATIONS WITHOUT METHACRYLOXYPROPYL TERMINATED DIMETHYLSILOXANE DILUENT

| Ingredient | Weight % |
|---|---|
| Photocurable Copolymer Represented by Formula (III), wherein the methacryloxypropyl-methysiloxane repeating unit represented by formula (I) constitutes from about 2% to about 4% or from about 7% to about 9% by mol of the copolymer | 80-99%, 90-99%, 95-99%, or 98-99% |
| Photoinitiator selected from phenylbis(2,4,6-trimethylbenzoyl)phosphine oxide, diphenyl-(2,4,6, trimethylbenzoyl)phosphine oxide (TPO), ethyl (2,4,6-trimethylbenzoyl)phenylphosphinate (TPO-L), or a combination thereof | 0.01-10%, 0.1-10%, 0.1-1%, or about 0.8% |
| Photoabsorber selected from 1-(Phenyldiazenyl)naphthalen-2-ol (Sudan I), 1-(2,4-Dimethylphenylazo)-2-naphthol (Sudan II), morin hydrate, coumarin 102, curcumin, or a combination thereof | 0.01-5%, 0.01-1%, 0.01-0.5%, about 0.05%, about 0.09%, or about 0.2% |
| Photosensitizer selected from 2-chloro-thioxanthone, isopropylthioxanthone (ITX), or a combination thereof | 0.01-5%, 0.05-5%, 0.1-1%, 0.3-1%, or about 0.4% |
| Hydrophillic additive (optional) | 0.01-20%, 0.05-2%, or about 1% |

TABLE 3

EXEMPLARY RESIN FORMULATIONS WITH METHACRYLOXYPROPYL TERMINATED DIMETHYLSILOXANE DILUENT

| Ingredient | Weight % |
| --- | --- |
| Photocurable Copolymer Represented by Formula (III), wherein the methacryloxypropyl-methysiloxane repeating unit represented by formula (I) constitutes from about 2% to about 4% or from about 7% to about 9% by mol of the copolymer | 5-99%, 5-30%, 20-40%, or 5-10% |
| Methacryloxypropyl terminated dimethyl siloxane represented by formula (IV) | 10-95%, 50-95%, or 70-90% |
| Photoinitiator selected from phenylbis(2,4,6-trimethylbenzoyl)phosphine oxide, diphenyl-(2,4,6, trimethylbenzoyl)phosphine oxide (TPO), ethyl (2,4,6-trimethylbenzoyl)phenylphosphinate (TPO-L), or a combination thereof | 0.01-10%, 0.1-10%, 0.1-1%, or about 0.8% |
| Photoabsorber selected from 1-(Phenyldiazenyl)naphthalen-2-ol (Sudan I), 1-(2,4-Dimethylphenylazo)-2-naphthol (Sudan II), morin hydrate, coumarin 102, curcumin, or a combination thereof | 0.01-5%, 0.01-1%, 0.01-0.5%, about 0.05%, about 0.09%, or about 0.2% |
| Photosensitizer selected from 2-chloro-thioxanthone, isopropylthioxanthone (ITX), or a combination thereof | 0.01-5%, 0.05-5%, 0.1-1%, 0.3-1%, or about 0.4% |
| Hydrophillic additive (optional) | 0.01-20%, 0.05-2%, or about 1% |

In one aspect, an exemplary photocurable resin comprises: (a) 0.01-10% (e.g., 0.05-1%, 0.1-1%, 0.2-1%, 0.3-1%, 0.5-1%, 0.6-1%, or about 0.8%) by weight of TPO-L; (b) 0.01-5% (e.g., 0.02-2%, 0.03-1%, 0.04-0.06%, or about 0.05%) by weight of Sudan I; (c) 0.01%-5% (e.g., 0.01-1%, 0.01-0.5%, or about 0.4%) by weight of ITX; (d) 80-99% (e.g., 90-99%, 95-99%, or 98-99%) by weight of a copolymer having a methacryloxypropyl-methysiloxane repeating unit represented by formula (I):

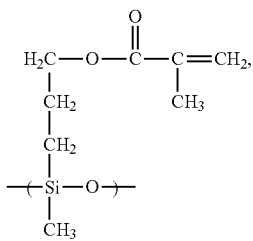

and a dimethylsilsiloxane repeating unit represented by formula (II):

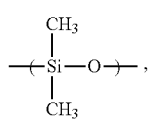

wherein the methacryloxypropyl-methysiloxane repeating unit constitutes 1-10 mol % (e.g., 2-4 mol % or 7-9%) of the copolymer, and the dimethylsiloxane repeating unit constitutes the balance of the mol %; and wherein the copolymer has a viscosity average molecular weight ($M_v$) ranging from about 20 kDa to about 60 kDa (e.g., 30 kDa to 60 kDa, 40 kDa to 60 kDa, or 50 kDa to 60 kDa). Optionally, this exemplarly photocurable resin can comprise in some aspects up to 2% by weight of a hydrophillic additive (e.g., a dimethylsiloxane-(ethylene oxide) block copolymer comprising 60-70 mol % ethylene oxide or 2-methacryloyloxyethyl phosphorylcholine (MPC)). In some aspects, this exemplary photocurable resin consists essentially of or consists of the above components.

In a further aspect, an exemplary photocurable resin comprises: (a) 5-99% (e.g., 5-30%, 5-10%, or 20-30%) by weight of a copolymer having a methacryloxypropyl-methysiloxane repeating unit represented by formula (I):

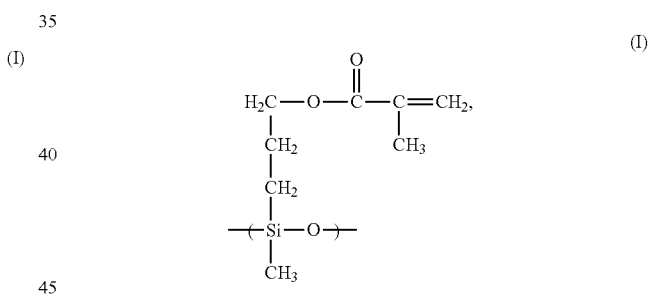

and a dimethylsiloxane repeating unit represented by formula (II):

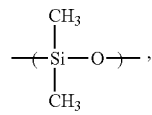

wherein the methacryloxypropyl-methysiloxane repeating unit constitutes 1-10 mol % (e.g., 2-4% or 7-9%) of the copolymer, and the dimethylsiloxane repeating unit constitutes the balance of the mol % of the copolymer, and wherein the copolymer has a viscosity average molecular weight ($M_v$) ranging from about 20 kDa to about 60 kDa (e.g., 30 kDa to 60 kDa, 40 kDa to 60 kDa, or 50 kDa to 60 kDa); (b) 10-95% (e.g., 60-95%, 80-95%, 60-75%) by weight of a methacryloxypropyl terminated dimethylsiloxane represented by formula (IV):

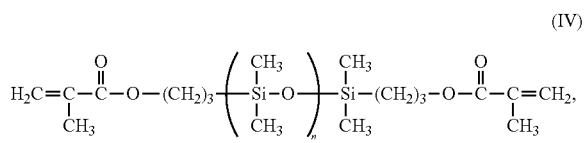

wherein n is an integer ranging from 1 to 350 (e.g., 120-140, or 130); (c) 0.01-10% (e.g., 0.05-1%, 0.1-1%, 0.2-1%, 0.3-1%, 0.5-1%, 0.6-1%, or about 0.8%) by weight of TPO-L; (d) 0.01-20% (e.g., 0.01-10%, 0.01-5%, 0.01-2%, or about 1%) of a (i) dimethylsiloxane-(ethylene oxide) block copolymer comprising 60-70 mol % ethylene oxide (e.g., having a molecular weight ranging from 400-1,500 g/mol, 400-800 g/mol, or 500-700 g/mol) or (ii) 2-methacryloyloxyethyl phosphorylcholine (MPC); (d) (b) 0.01-5% (e.g., 0.02-2%, 0.03-1%, 0.04-0.06%, or about 0.05%) by weight of Sudan I; (e) 0.01%-5% (e.g., 0.01-1%, 0.01-0.5%, or about 0.4%) by weight of ITX. Optionally, this exemplarly photocurable resin can comprise in some aspects up to 2% by weight of a hydrophillic additive (e.g., a dimethylsiloxane-(ethylene oxide) block copolymer comprising 60-70 mol % ethylene oxide or 2-methacryloyloxyethyl phosphorylcholine (MPC)). In some aspects, this exemplary photocurable resin consists essentially of or consists of the above components.

C. 3-D Printing Methods

Also disclosed herein is a method of stereolithographically printing a 3-D object using a disclosed photocurable resin. In one aspect, the method for printing the 3-D object comprises (a) providing a disclosed photocurable resin, (b) selectively photopolymerizing a first portion of the resin to provide a first photocured layer, and (c) selectively photopolymerizing a second portion of the resin to provide a second photocured layer, wherein the first and second photocured layers form an integral photocured layer. In a further aspect, steps (b) and (c) can be sequentially repeated until the 3-D object is printed.

Also disclosed herein is an improved in a method for stereolithographically printing a 3-D object, the improvement comprising the use of a disclosed photocurable resin.

In a further aspect, the method of stereolithographically printing the 3-D object comprises (a) providing a vessel comprising a disclosed photocurable resin; (b) positioning a build surface on which the object is to be printed at a distance on a vertical Z-axis from the bottom on the vessel; (c) selectively photopolymerizing a first portion of the resin to provide a first photocured layer adjacent to the build surface; (d) adjusting the distance of the build surface on the vertical Z-axis either closer to or farther away from the bottom of the vessel (depending on whether the object is being printing bottom-up or top-down); (e) selectively photopolymerizing a second portion of the resin to provide a second photocured layer, wherein the first and second photocured layers form an integral photocured layer; and (f) sequentially repeating steps (d) and (e) until the object is printed.

The photocurable resin can be used with a variety of 3-D printing methods. In one aspect, the photocurable resin can be used with a laser galvanometer method for 3-D printing. In a further aspect, the photocurable resin can be used with various stereolithographic methods for 3-D printing, including for example the Nanoscribe Photonic Professional GT2 system and other systems that use two-photon polymerization (2PP) to produce 3-D objects. The photocurable resin can also be used with CLIP printing systems such as Carbon DLS printers. Other suitable printing systems are those that use LEDs for digital-light projection (DLP). Still other suitable printing systems include micro-precision 3-D printers that use projection micro stereolithography technology.

In one aspect, for example, with reference to FIG. 1, which depicts a commercially-available 3-D stereolithographic printer, the 3-D object can be stereolithographically printed using the 3-D printer (100) through a top-down approach. The photocurable resin can be poured into the vessel (110). To ensure adhesion of the object to the build platform (120) having the build surface, a glass slide silanized with 3-(trimethoxysilyl)propyl methacrylate can be secured to the build surface by applying an adhesive to one side of the glass and attaching the slide to the build surface. For example, the adhesive can be UV-curable, and once applied to the slide, the adhesive can be cured by exposing the slide to UV light to attach the slide to the build surface. The build platform (120) can then be lowered until it touches the photocurable resin in the vessel (110). A digital light projector (DLP) can be used to project the first slice of the object for a predetermined amount of time as the light source of the 3-D printer selectively photopolymerizes the resin. The build surface then raises and lowers, the DLP projects the second slice of the object, and the process continues until the 3-D object is printed. A bottom-up approach can similarly be used, where the build surface progressively lowers into the vessel (progressively submerged into the photocurable resin) until the 3-D object is printed on the build surface.

The 3-D printed object can be removed from the build surface, rinsed with solvents and/or cleaned with pressurized air. Typically, the object can be exposed to additional UV light for an amount of time to ensure sufficient curing. Any uncured material on the object can be washed away with a suitable solvent. Alcohols, such as isopropyl alcohol, can be used to wash away any solvents used for washing the cured 3-D object after uncured resin is removed.

D. 3-D Objects Printed from a Disclosed Resin

The 3-D objects that can be printed using a disclosed method include solid objects or objects with one or more voids, e.g., coplanar XY channels, or 3D channels connecting on the object's vertical Z-axis. 3-D objects can be designed using 3D-CAD software, which can be exported to a suitable 3-D printer to print the object. Surprisingly, the inventors discovered that through the use of a disclosed resin, 3-D objects can be printed that have a variety of feature sizes, including those having a size about 20 microns or less.

In one aspect, the 3-D object printed from a disclosed photocurable resin can be a microfluidic device. In a further aspect, the 3-D object printed using a disclosed photocurable resin can be a microfluidic artificial lung. In one aspect, the 3-D object can be a microfluidic device such as an artificial lung comprising one or more flow channels or conduits having a diameter or height of 120 microns or less, e.g., from about 20 microns to about 120 microns, or from about 20 microns to about 60 microns, and also including those having a diameter or height of less than about 20 microns.

In other aspects, the 3-D printed object can be a microfluidic device with a high surface area to volume ratio and with small channel diameters or heights, e.g., less than about 120 microns, including without limitation artificial organs, lab-on-a-chip devices, small volume reaction chambers, cell growth chambers, gas separation devices, diffusion systems, and the like. In a further aspect, the 3-D object printed from a disclosed photocurable resin can be a microfluidic artificial organ or extracorporeal support device, including without limitation an artificial lung, kidney, liver, among others.

In one aspect, the photocurable resin can be used to prepare a microfluidic artificial lung. In various aspects, the microfluidic artificial lung prepared from a disclosed photocurable resin can comprise a blood inlet and outlet and an air inlet and outlet in fluid communication with one or more micron-sized flow channels or conduits, such as a flow channel or conduit having a channel diameter or height in the range of about 20 microns to about 120 microns, e.g., from about 20 microns to about 60 microns, but also including those having a channel diameter or height of about 20 microns or less.

In a further aspect, the microfluidic artificial lung can comprise a first channel or conduit for transporting gas, e.g., oxygen, and a second channel or conduit for transporting a liquid, e.g., blood. The first and second channels or conduits can be part of a first network of channels or conduits for transporting gas such as oxygen and a second network of channels or conduits for transporting a liquid such as blood, artificial blood, or another liquid depending on the desired application. In one aspect, the first channel or conduit network can be arranged to facilitate the exchange of oxygen and carbon dioxide to and/or from the second channel or conduit network. The first channel or conduit network, for example, can be adjacent to or in close proximity with the second channel or conduit network. In a further aspect, the first and second channel or conduit networks can be separated by a thin membrane that allows for diffusion and gas exchange.

E. Examples

The following examples are put forth so as to provide those of ordinary skill in the art with a complete disclosure and description of how the methods and products claimed herein are made and evaluated, and are intended to be purely exemplary and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° F. or is at ambient temperature, and pressure is at or near atmospheric. The Examples are provided herein to illustrate the invention, and should not be construed as limiting the invention in any way.

1. Photocurable Resin Formulation

Resin components were weighed out separately on a Sartorius Analytical Balance according to the following w/w % of material: 98.6 w/w % [7-9% (Methacryloxypropyl) methylsiloxane]-dimethylsiloxane copolymer, 0.8 w/w % TPO-L, 0.4 w/w % ITX, and 0.2 w/w % Sudan I. In some iterations of the resin formulas the side-chain copolymer, [7-9% (Methacryloxypropyl)methylsiloxane]-dimethylsiloxane copolymer (RMS-083) is replaced with [2-4% (Methacryloxypropyl)methylsiloxane]-dimethylsiloxane copolymer (RMS-033). In cases where the resin formula included the addition of the end-chain copolymer, Methacryloxypropyl terminated polydimethylsiloxane (DMS-R22), the amount of the side-chain copolymer was reduced by the corresponding w/w %. Similarly, in formulas where the amount of photoabsorber or photosensitizer was adjusted, the corresponding w/w % of side-chain polymer was adjusted in the formulation. Components were combined, mixed by hand, heated for at least two hours at 70° C., and then sonicated with the Qsonica Q700 sonicator to ensure uniform mixing and particle size reduction. Sudan I was purchased from Sigma Aldrich. 2-Isopropylthioxanthone ≥98.0% was purchased from VWR International. [7-9% (Methacryloxypropyl)methylsiloxane]-dimethylsiloxane copolymer (RMS-083), [2-4% (Methacryloxypropyl) methylsiloxane]-dimethylsiloxane copolymer (RMS-033), and Methacryloxypropyl terminated polydimethylsiloxane (DMS-R22) were purchased from Gelest, Inc. 2,4,6-Trimethyl benzoyl diphenyl phosphine oxide (TPO-L) was purchased from PL Industries of Esstech, Inc. All materials were used as received.

2. Photocurable Resin Characterization

Resin characterization was performed using the "spot testing method" described by Asiga for the creation of a material ini file. Uncured resin was placed on a glass slide and cured by exposing a small circle of light from the printer (Asiga MAX X27 UV) at 15 mW/cm^2 and at various time points. The excess, uncured resin was rinsed from the glass slide with IPA (2-Propanol, Laboratory Reagent, ≥99.5% purchased from Sigma Aldrich). The thickness of the cured resin was measured by taking side view images of the cured spot with the Dino-Lite Digital Microscope using the DinoCapture 2.0 software. The relationship between cure energy and cure thickness was input to the material ini file for printing with the Asiga MAX X27 UV printer.

Figure 2:
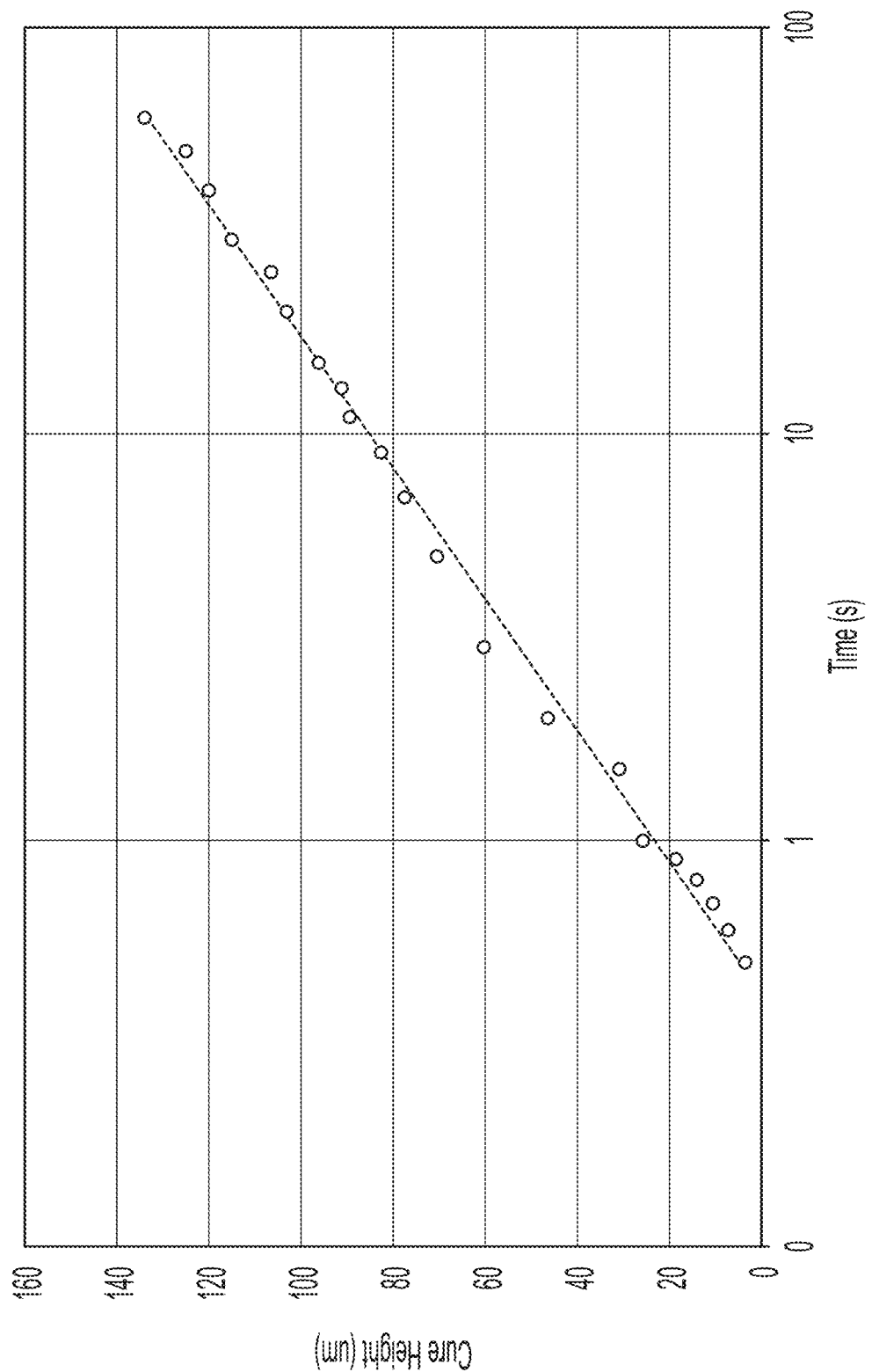
FIG. 2 shows a working curve of photocurable resin taken at an optical dose of 27 mW/cm² on an Asiga MAX 27X UV printer.

A working curve was created to determine the characteristic polymerization depth, $z_p$, of the resin given the optical dose from the printer. The curve was created by exposing UV light to uncured resin at a constant light intensity (27 mW/cm2) for a series of timepoints. Thickness measurements of the cured material at each corresponding timepoint were taken and the curve was produced. One example of this curve is shown in FIG. 2, for a resin having 98.6 w/w % copolymer ([7-9% (Methacryloxypropyl)methylsiloxane]-dimethylsiloxane) (RMS-083), 0.8 w/w % TPO-L, 0.4 w/w % ITX, and 0.2 w/w % Sudan I.

The characteristic polymerization depth is defined as:

$$z_p = h_a \ln\left(\frac{t_p}{T_c}\right),$$

where $h_a$=1/absorbance of the resin, $t_p$ is the time it takes for the resin to reach a polymerized state (uncured to cured) at depth $z_p$, and $T_c$ is the time it takes to reach a polymerized state at initial exposure ($z_p$=0).

Using this equation and the curve in FIG. 2, $h_a$ (the slope of the curve) and $T_c$ (the x-intercept) can be defined to predict the polymerization depth, $z_p$, of the material for a given optical dose at time, $t_p$. Keeping optical dose constant, for a smaller $h_a$ (larger absorbance) the polymerization depth decreases, improving cure resolution. This analysis illustrates the relationship between absorbance of the material and polymerization depth, ultimately describing the resolution performance of the resin.

3. 3-D Printing

All resin characterization and builds were printed using the commercially available Asiga MAX X27 UV printer (purchased through ProtoProducts). This printer uses DLP technology with a 385 nm light source and a pixel resolution of 27 um and Z (vertical) resolution of 1 um. Asiga Composer Software was used as the interface for the handling of STL files and controlling print parameters. All 3D models were generated in SOLIDWORKS and exported to an STL file format.

To ensure adhesion of the build to the build platform, printing was done with a silanized glass slide. The glass slide was silanized with 3-(trimethoxysilyl)propyl methacrylate (purchased from Sigma Aldrich) following the procedure as described by A. Urrios, et. al Lab Chip 2016, 16, 2287. The glass slide was secured to the build platform by applying a thin layer of Protoglass (purchased from ProtoProducts) to one side of the glass, attaching the slide to the build platform, and exposing UV light to glue the slide.

Figure 3:
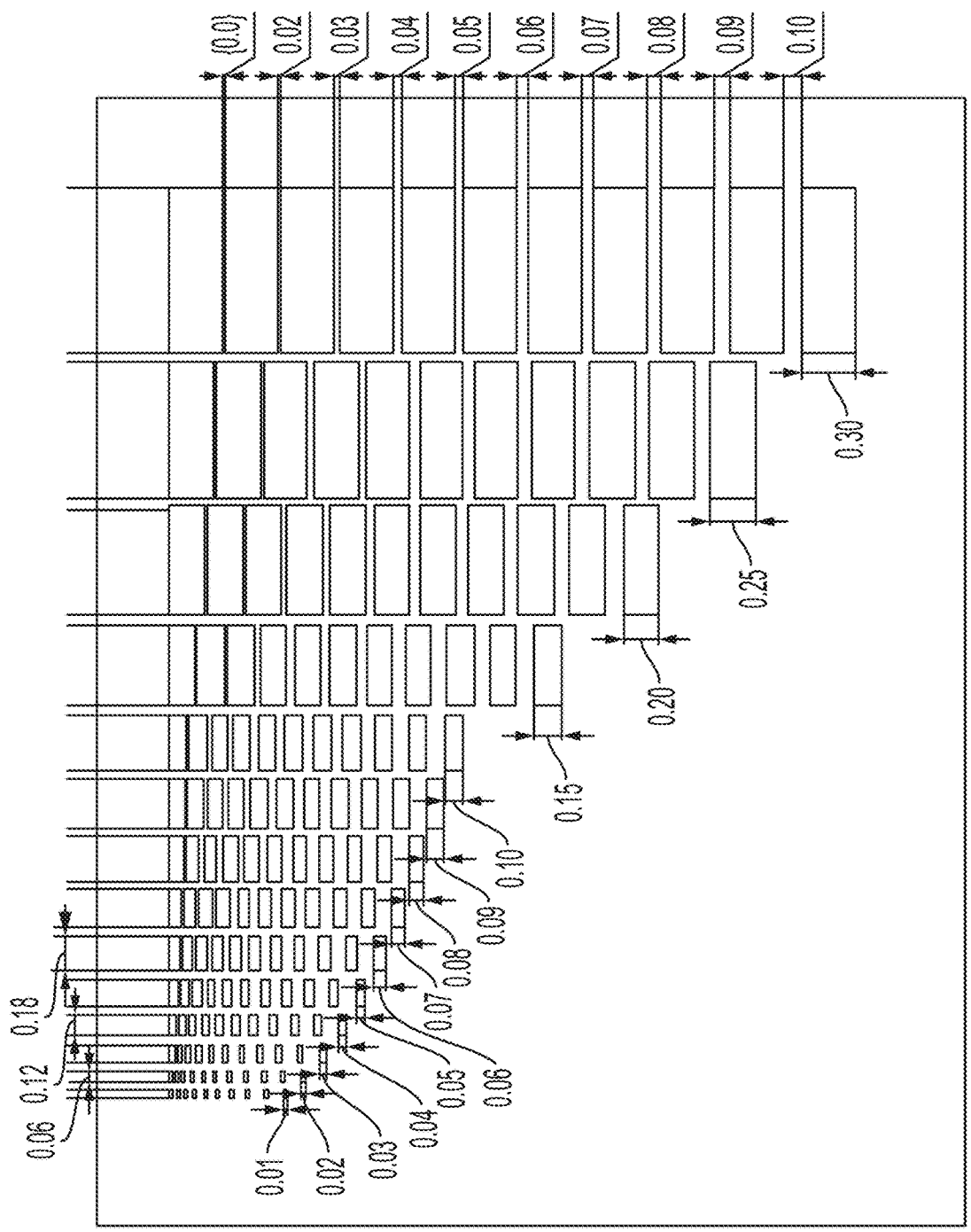
FIG. 3 shows a front view of a 3-D structure drawn in SOLIDWORKS design software. Channel heights range from 10-300 μm and membranes range from 10-100 μm.

To further characterize the Z resolution of the resin, a structure (shown in FIG. 3) was designed with an array of channels with varying heights and membranes with varying thicknesses, and the structure was printed. The build was then washed with IPA to remove most of the uncured resin and compressed air was used to clear the remaining liquid resin from the channels. Channel heights and membranes were measured on the Dino-Lite Digital Microscope.

Figure 4A:
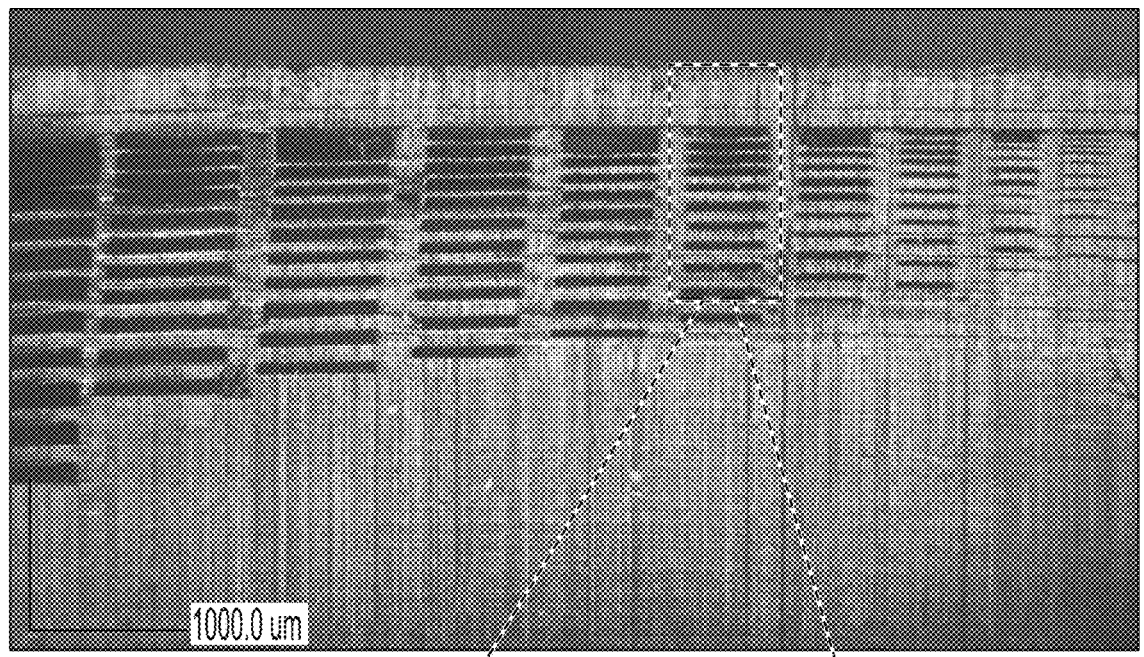
FIG. 4A shows a structure with microchannels of varying heights and membrane thicknesses to characterize resolution.
Figure 4B:
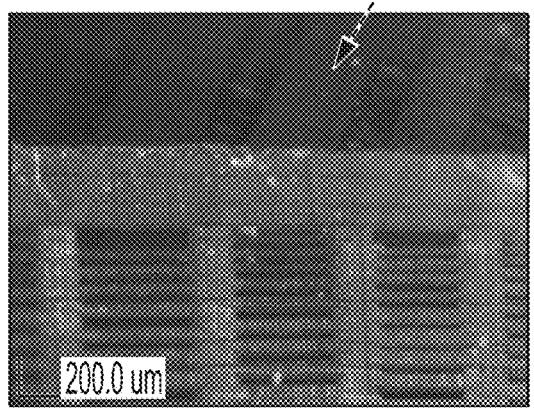
FIG. 4B shows an expanded view of a section of microchannels shown in FIG. 4A.
Figure 4C:
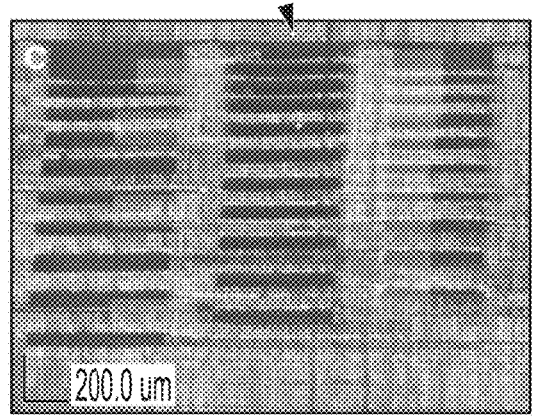
FIG. 4C shows another expanded view of a section of microchannels shown in FIG. 4A.

This structure was 3D printed to investigate resin printing capabilities while optimizing printer specific parameters. Using this approach, channel heights as small as 60 microns tall and membranes as thin as 20 microns (see FIG. 4) were realized. The resolution achieved using the disclosed photocurable resin is surprisingly and unexpectedly superior to known photocurable resins, including those listed in Table 4.

TABLE 4

| Reference | Membrane Thickness | Channel Height | Resin |
|---|---|---|---|
| Kuo, A. P. et. al. (2019), Advanced Materials Technologies, 4 (6), 1, 800395 | 50 μm | 500 μm | Polyethylene glycol diacrylate (PEGDA) |
| Gong, H. et al. (2017), Lab on a Chip 17 (17), 2899-2909 | N/A | 18 μm | Polyethylene glycol diacrylate (PEGDA) |
| Bhattacharjee, N. et al. (2018), Advanced Materials, 30 (22), 1800001 | 220 μm | 2000 μm | Poly(dimethylsiloxane) based polymer (PDMS) |
| N/A-Disclosed photocurable resin | 20 μm | 60 μm | 98.6 w/w % [7-9% (Methacryloxypropyl) methylsiloxane]-dimethylsiloxane copolymer (RMS-083), 0.8 w/w % TPO-L, 0.4 w/w % ITX, and 0.2 or 0.05 w/w % Sudan I |

4. Material Performance

Figure 5:
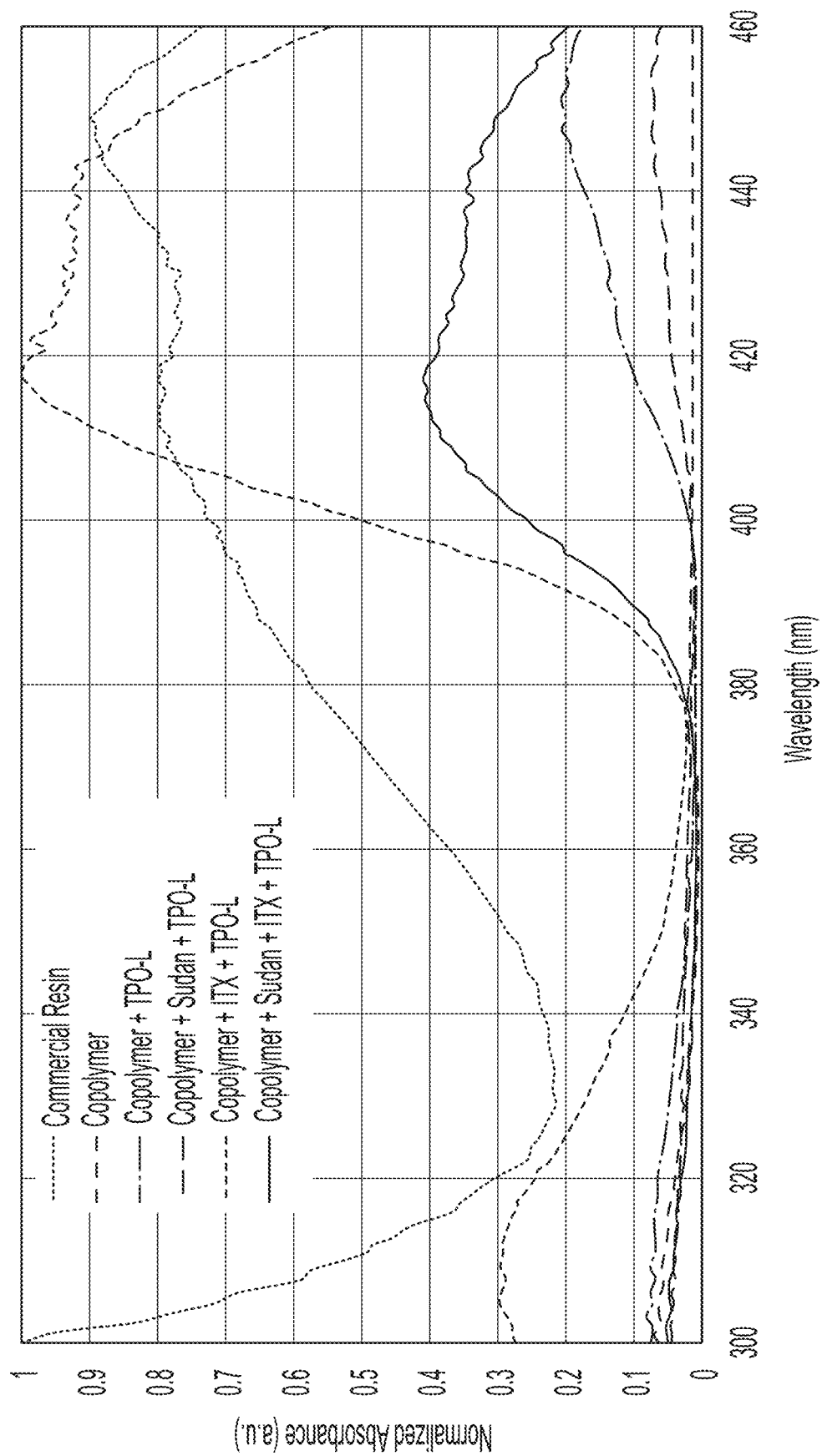
FIG. 5 is a plot showing absorbance data for an exemplary resin formulation.

Material absorbance data were taken using a spectrophotometer. Triplicates of each sample were measured and analyzed for the following samples (FIG. 5): 100 w/w % [7-9% (Methacryloxypropyl)methylsiloxane]-dimethylsiloxane copolymer (RMS-083); 99.2 w/w % [7-9% (Methacryloxypropyl)methylsiloxane]-dimethylsiloxane copolymer (RMS-083)+0.8 w/w % TPO-L (photoinitiator); commercially sold resin for Asiga MAX 27X UV printer; 98.8 w/w % [7-9% (Methacryloxypropyl)methylsiloxane]-dimethylsiloxane copolymer (RMS-083)+0.8 w/w % TPO-L+0.4 w/w % ITX; 99.0 w/w % [7-9% (Methacryloxypropyl)methylsiloxane]-dimethylsiloxane copolymer (RMS-083) +TPO-L +Sudan I; 98.6 w/w % [7-9% (Methacryloxypropyl)methylsiloxane]-dimethylsiloxane copolymer (RMS-083)+0.8 w/w % TPO-L+0.4 w/w % ITX+0.2 w/w % Sudan I.

Absorbance spectra of a resin shows the curing compatibility with a 3D printer. Overlap of the material spectrum and the spectrum of the printer's optical source is important for an adequate photopolymerization reaction to occur. These results also reveal the influence of the photoabsorber to fine tune the absorbance properties of the material.

Figure 6:
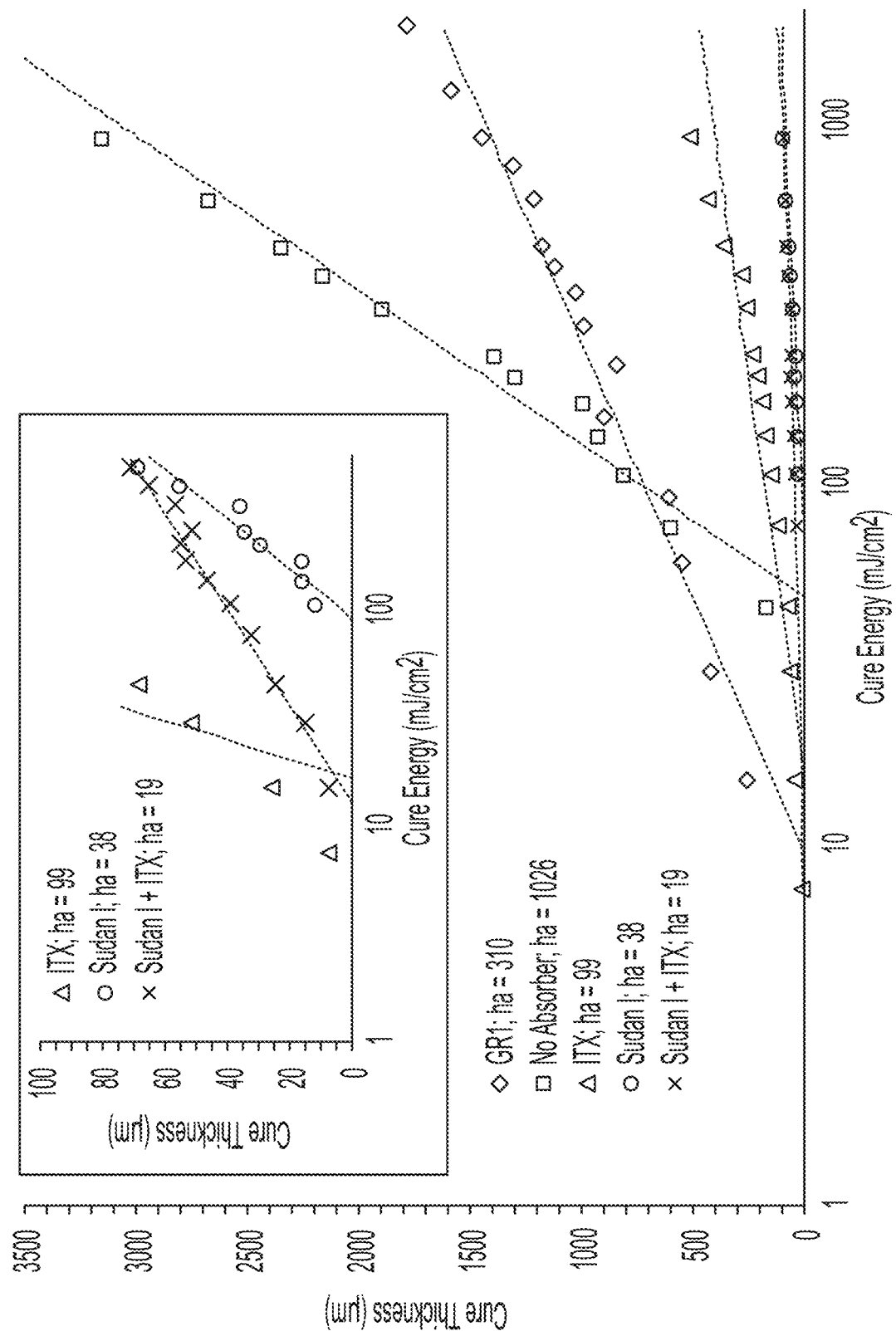
FIG. 6 is a plot of cure thickness of the resin versus cure energy from the UV light of an ASIGA 3-D stereolithographic printer. As shown, by combining Sudan I and ITX, printing resolution increased 10-fold relative to a commercially-available, high-resolution GR1 resin. The Sudan I+ITX curve (cross) has the following formulation: 0.2 w/w % Sudan I, 0.4 w/w % ITX, 0.8 w/w % TPO-L, and 98.6 w/w % [7-9% (Methacryloxypropyl)methylsiloxane]-dimethylsiloxane copolymer (RMS-083). The Sudan I curve (circle) has the following formulation: 0.2 w/w % Sudan I, 0.8 w/w % TPO-L, and 90.0 w/w % [7-9% (Methacryloxypropyl)methylsiloxane]-dimethylsiloxane copolymer (RMS-083). The ITX curve (triangle) has the following formulation: 0.4 w/w % ITX, 0.8 w/w % TPO-L, and 98.8 w/w % [7-9% (Methacryloxypropyl)methylsiloxane]-dimethylsiloxane copolymer (RMS-083). The No Absorber curve (square) was generated from the following formulation: 0.8 w/w % TPO-L and 99.2 w/w % copolymer. The GR1 Clear resin (diamond) was obtained from ProtoProducts and was formulated for intended use with the Asiga MAX series printers with a 385 nm LED light source.

As shown in FIG. 6, printing resolution improved using a combination of Sudan I as a photoabsorber and ITX as a photosensitizer relative to a formulation without ITX and relative to a formulation with no photoabsorber. FIG. 6 also demonstrates that through the use of a disclosed photocurable resin, printing resolution increased by 10-fold relative to that achieved with a commercially-available, high-resolution GR1 resin.

Figure 7:
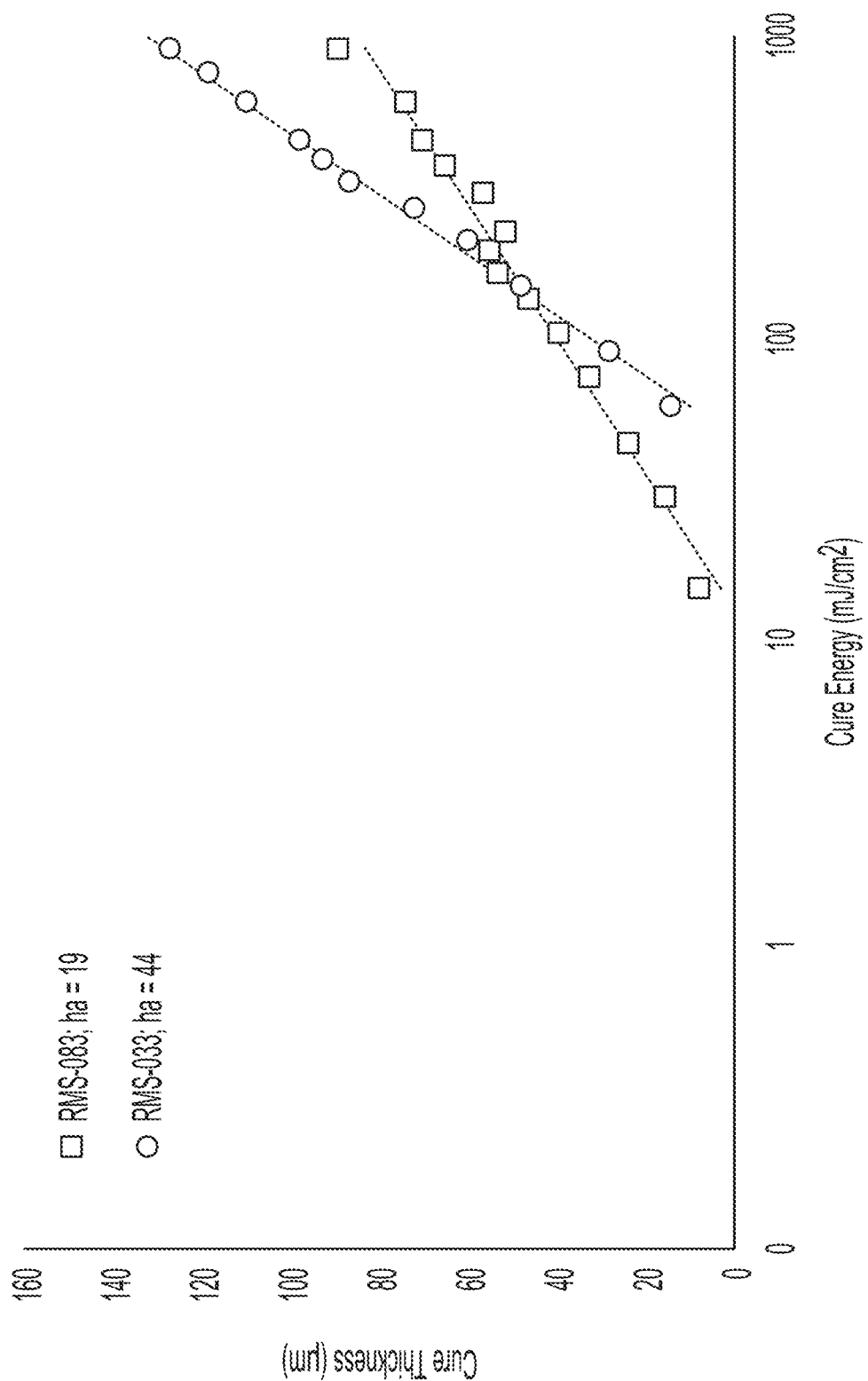
FIG. 7 is a plot of cure thickness of the resin versus cure energy from the UV light of an ASIGA 3-D stereolithographic printer. The curves here illustrate formulations with Sudan I and ITX for each copolymer, RMS-083 (square) and RMS-033 (circle). RMS-083 corresponds to [7-9% (Methacryloxypropyl)methylsiloxane]-dimethylsiloxane copolymer, while RMS-033 corresponds to [2-4% (Methacryloxypropyl)methylsiloxane]-dimethylsiloxane copolymer. Both copolymers are commercially available from Gelest. The solubility limit of Sudan I in RMS-033 is less than RMS-083, which can in some aspects restrict the resolution capabilities of RMS-033. This is further demonstrated in the larger $h_a$ value for RMS-033, where $h_a$=1/absorbance of the material. Therefore, larger $h_a$ equates to smaller absorbance and consequently smaller resolution capabilities of the resin. RMS-083 produces a more brittle polymer when cured. The Sudan RMS-083 curve (square) has the following formulation: 0.2 w/w % Sudan I, 0.4 w/w % ITX, 0.8 w/w % TPO-L, and 98.6 w/w % RMS-083 copolymer. The RMS-033 curve (circle) has the following formulation: 0.05 w/w % Sudan I, 0.4% ITX, 0.8 w/w % TPO-L, and 98.75 w/w % RMS-033 copolymer.

FIG. 7 is a is a plot of cure thickness of the resin versus cure energy from the UV light of an ASIGA 3-D stereolithographic printer. The curve shown in FIG. 7 illustrates an optimal resin formulation with Sudan I for each copolymer, [7-9% (Methacryloxypropyl)methylsiloxane]-dimethylsiloxane copolymer (RMS-083) (square) and [2-4% (Methacryloxypropyl)methylsiloxane]-dimethylsiloxane copolymer (RMS-033) (circle). The solubility limit of Sudan I in RMS-033 is less than RMS-083, restricting the resolution capabilities of RMS-033. This is further demonstrated in the larger $h_a$ value for RMS-033, where $h_a$=1/absorbance of the material. Therefore, larger $h_a$=smaller absorbance and consequently smaller resolution capabilities of the resin. The Sudan RMS-083 curve (square) has the following formulation: 0.2 w/w % Sudan I, 0.4 w/w % ITX, 0.8 w/w % TPO-L, and 98.6 w/w % copolymer. The RMS-033 curve (circle) has the following formulation: 0.05 w/w % Sudan I, 0.4% ITX, 0.8 w/w % TPO-L, and 98.7 w/w % copolymer.

Figure 8:
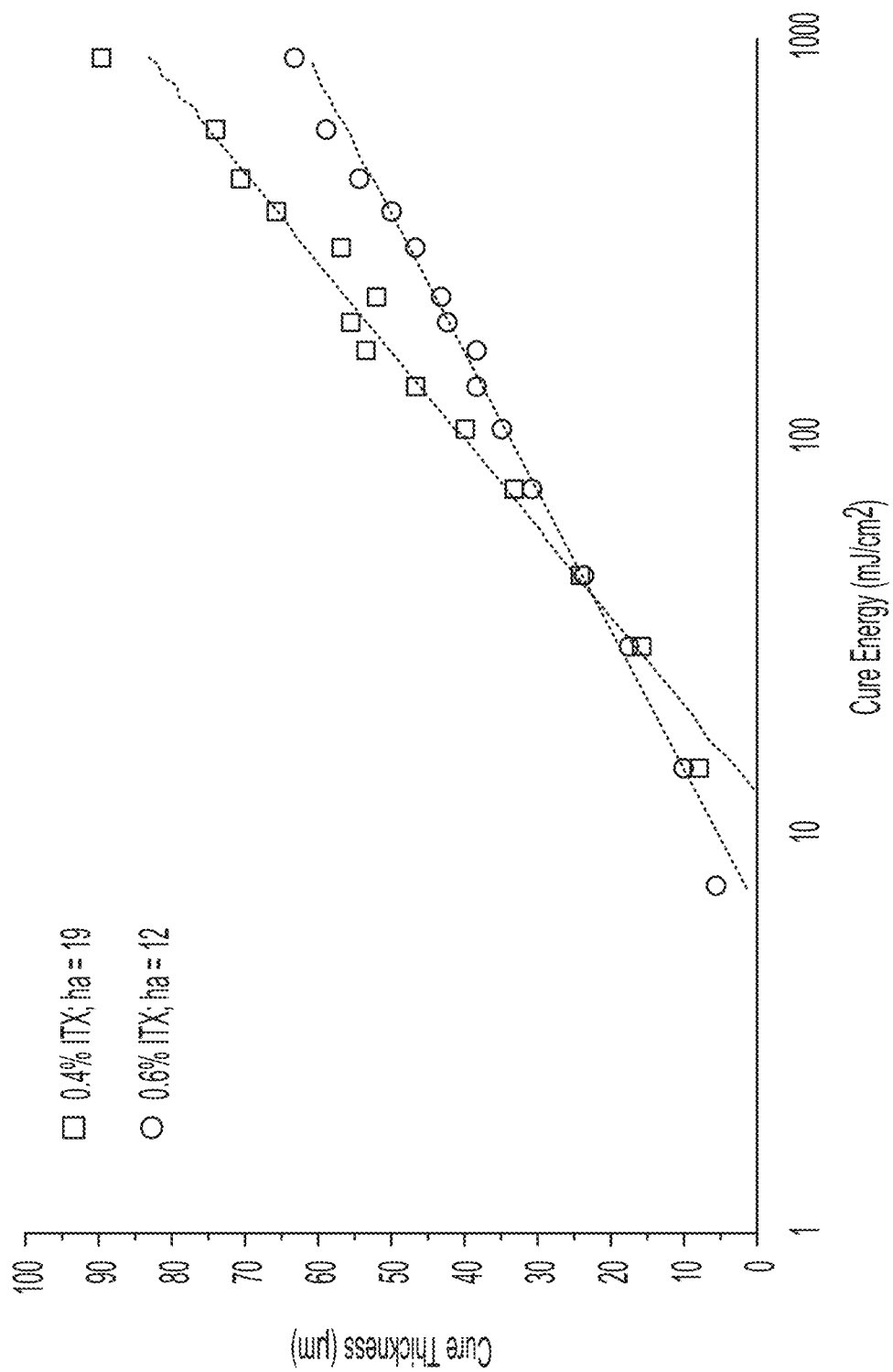
FIG. 8 is a plot of cure thickness of the resin versus cure energy from the UV light of an ASIGA 3-D stereolithographic printer. The 0.4% ITX curve (square) was generated from the following formulation: 0.2 w/w % Sudan I, 0.4 w/w % ITX, 0.8 w/w % TPO-L, and 98.6 w/w % [7-9% (Methacryloxypropyl)methylsiloxane]-dimethylsiloxane copolymer (RMS-083). The 0.6% ITX curve (circle) was generated from the following formulation: 0.2 w/w % Sudan I, 0.6% ITX, 0.8 w/w % TPO-L, and 98.4 w/w % [7-9% (Methacryloxypropyl)methylsiloxane]-dimethylsiloxane copolymer (RMS-083).

FIG. 8 is a plot of cure thickness of the resin versus cure energy from the UV light of an ASIGA 3-D stereolithographic printer. Increasing the w/w % of ITX increases resolution as demonstrated by the curves and is further validated by the smaller $h_a$ value, indicating larger absorbance of the resin. The 0.4% ITX curve (square) was generated from the following formulation: 0.2 w/w % Sudan I, 0.4 w/w % ITX, 0.8 w/w % TPO-L, and 98.6 w/w % copolymer RMS-083. The 0.6% ITX curve (circle) was generated from the following formulation: 0.2 w/w % Sudan I, 0.6% ITX, 0.8 w/w % TPO-L, and 98.4 w/w % RMS-083.

Figure 9:
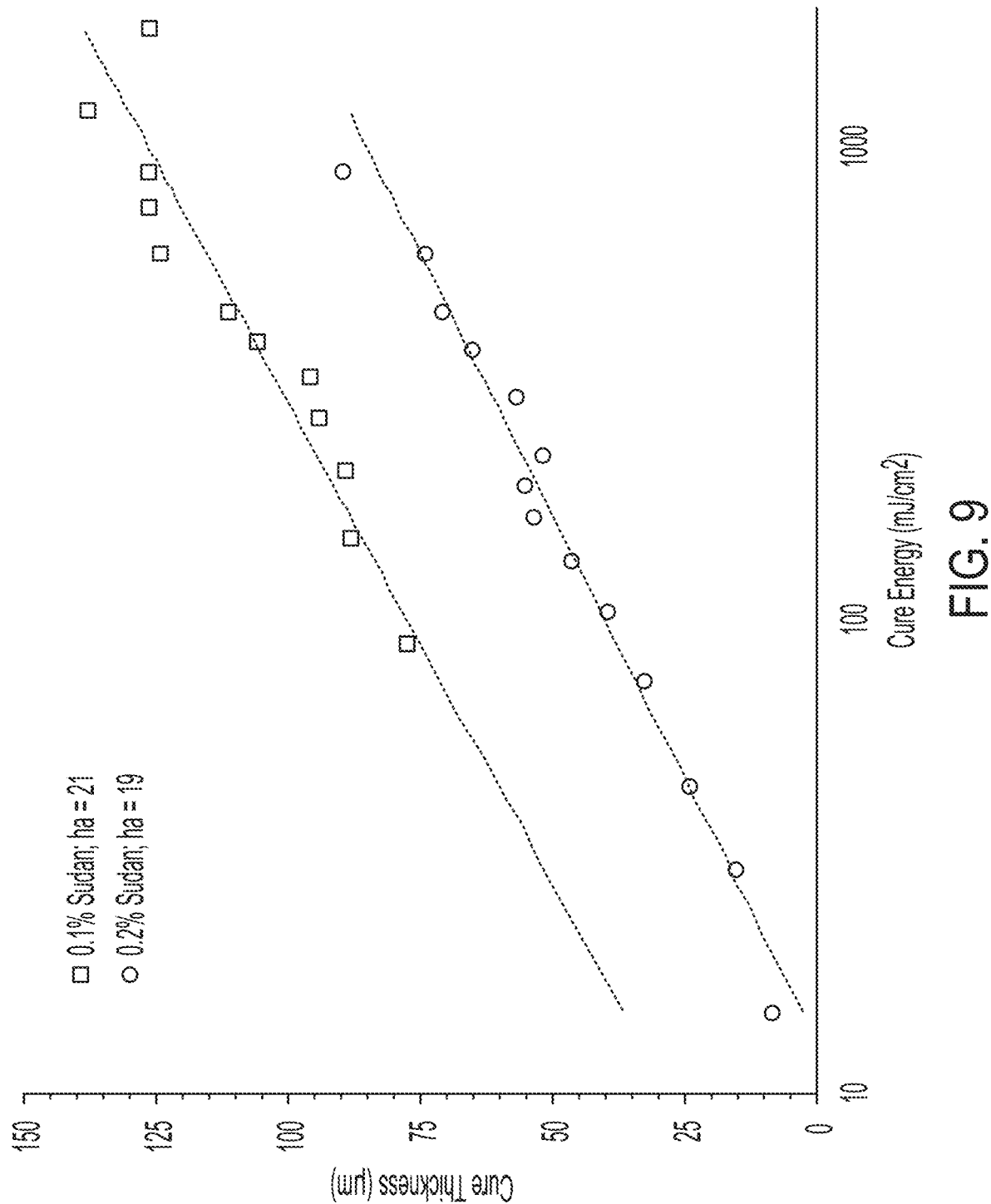
FIG. 9 is a plot of cure thickness of the resin versus cure energy from the UV light of an ASIGA 3-D stereolithographic printer. The 0.1% Sudan I curve (square) has the following formulation: 0.1 w/w % Sudan I, 0.4 w/w % ITX, 0.8 w/w % TPO-L, and 98.7 w/w % [7-9% (Methacryloxypropyl)methylsiloxane]-dimethylsiloxane copolymer (RMS-083). The 0.2% Sudan curve (circle) has the following formulation: 0.2 w/w % Sudan I, 0.4% ITX, 0.8 w/w % TPO-L, and 98.6 w/w % [7-9% (Methacryloxypropyl)methylsiloxane]-dimethylsiloxane copolymer (RMS-083).

FIG. 9 is a plot of cure thickness of the resin versus cure energy from the UV light of an ASIGA 3-D stereolithographic printer. The higher w/w % of Sudan I has a higher resolution as demonstrated in the curves and further validated by the smaller $h_a$ value. The 0.1% Sudan I curve (square) has the following formulation: 0.1 w/w % Sudan I, 0.4 w/w % ITX, 0.8 w/w % TPO-L, and 98.7 w/w % copolymer RMS-083. The 0.2% Sudan curve (circle) has the following formulation: 0.2 w/w % Sudan I, 0.4% ITX, 0.8 w/w % TPO-L, and 98.6 w/w % RMS-083.

(Prophetic) Mechanical properties of the material will be determined by 3D printing tensile test bars and performing mechanical testing on a universal testing machine. Relevant properties such as Young's modulus, tensile strength, fracture strength and elongation will be recorded and analyzed. Possible leaching of resin components could result in contamination depending on the end use of the 3D printed device. Following ASTM standard F619, specimens will be soaked in a saline solution for various timepoints (e.g. 2 h, 4 h, 8 h, 1 d, 2 d) and analysis of leached components can be measured by either/both absorbance measurement of isolated media containing leachables at a specified wavelength or via mass loss from the sample using a microanalytical balance. Gas permeability for the cured resin will be measured using a previously developed protocol from Thompson, A. J., et. al. (2017). Biomicrofluidics, 11(2), 024113.

Figure 10:
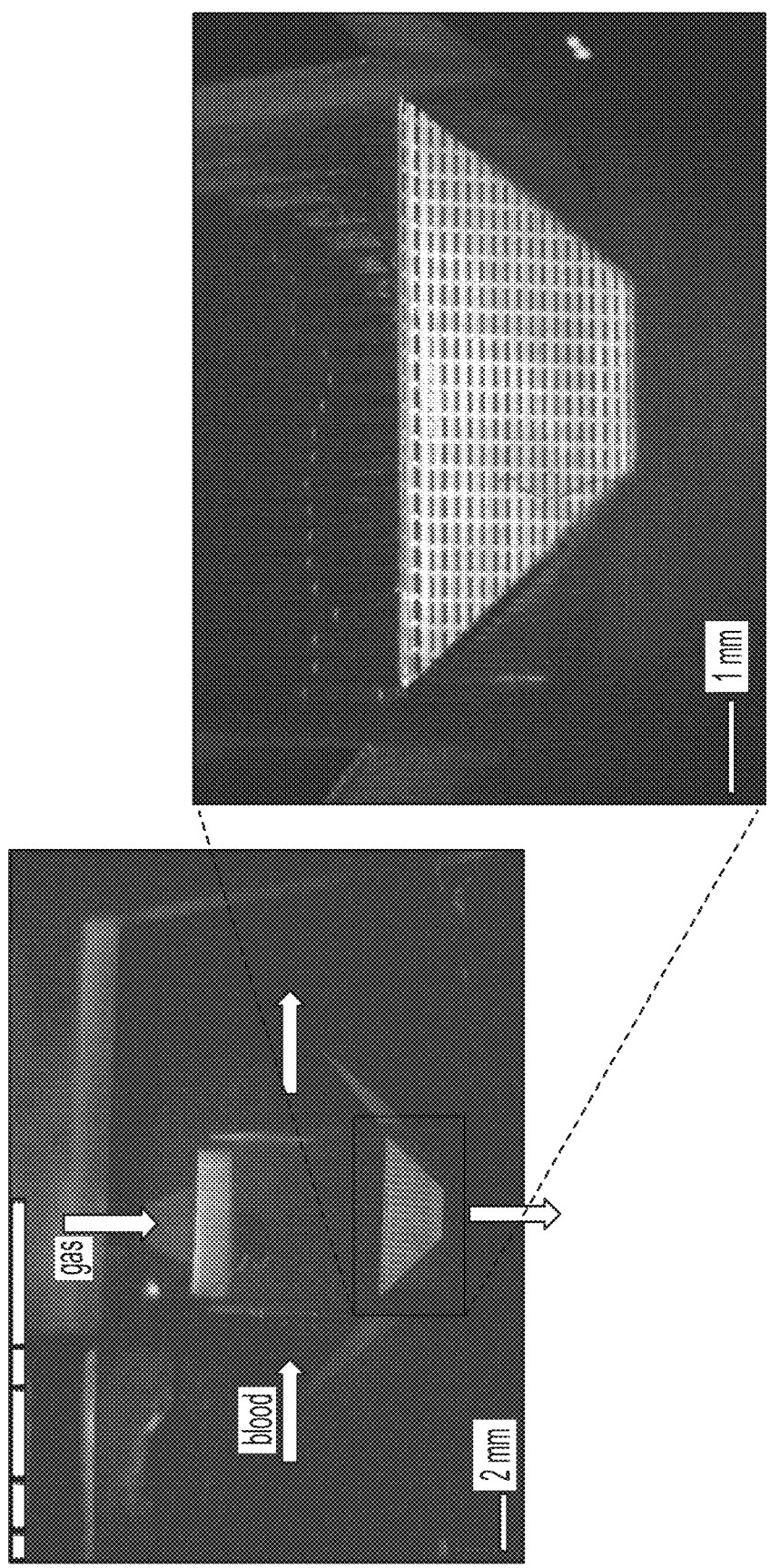
FIG. 10 is an image of a partially printed 3-D microfluidic artificial lung device with blood flow channels parallel to the page and gas flow channels into the page, allowing for the exchange of oxygen and carbon dioxide across a thin membrane.

With reference to FIG. 10, the disclosed photocurable resin can be used to prepare a microfluidic artificial lung. For example, FIG. 10 shows an image of a partially printed 3-D microfluidic artificial lung device with blood flow channels parallel to the page and gas flow channels into the page, allowing for the exchange of oxygen and carbon dioxide to and/or from the blood flow and gas flow channels.

Figure 11:
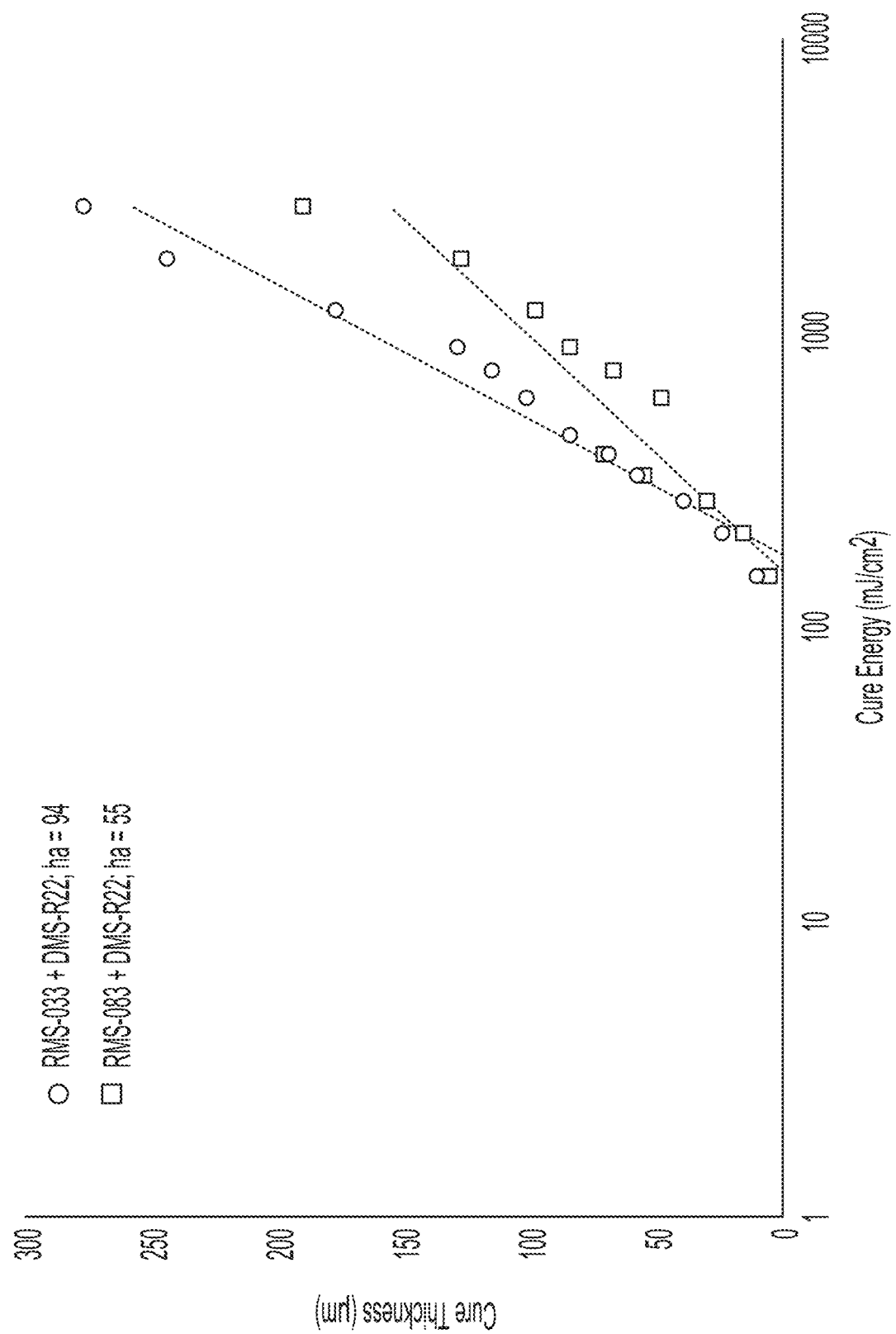
FIG. 11 shows a plot of cure thickness of an exemplary resin versus cure energy from the UV light of an ASIGA 3-D stereolithographic printer. The curves illustrate formulations with Sudan I and ITX for each combination of a methacryloxypropyl terminated dimethylsiloxane (DMS-R22, commercially-available from Gelest, CAS No. 58130-03-3) with RMS-083 (square) or RMS-033 (circle). The solubility limit of Sudan I in RMS-033 is less than RMS-083, which can in some aspects restrict the resolution capabilities of RMS-033. This is further demonstrated in the larger ha value for RMS-033, where ha=1/absorbance of the material. Therefore, larger ha=smaller absorbance and consequently smaller resolution capabilities of the resin. The Sudan RMS-083 curve (square) has the following formulation: 0.09 w/w % Sudan I, 0.4 w/w % ITX, 0.8 w/w % TPO-L, 90 w/w % DMS-R22 and 8.71 w/w % RMS-083 copolymer. The RMS-033 curve (circle) has the following formulation: 0.05 w/w % Sudan I, 0.4% ITX, 0.8 w/w % TPO-L, 70 w/w % DMS-R22, and 28.75 w/w % RMS-033 copolymer.

The resolution of some resin formulas is restricted by the solubility limit of the photoabsorbers and photosensitizers added to the copolymer. For example, in FIG. 11, Sudan I has a higher solubility limit in the copolymer RMS-083 and therefore has a larger w/w % of Sudan I in the resin and consequently better resolution capability. Given the solubility limits of the copolymers to maintain a uniform mixture, different w/w percentages and combinations of the photoabsorber and photosensitizer can be fine-tuned to maximize print resolution.

Figure 12:
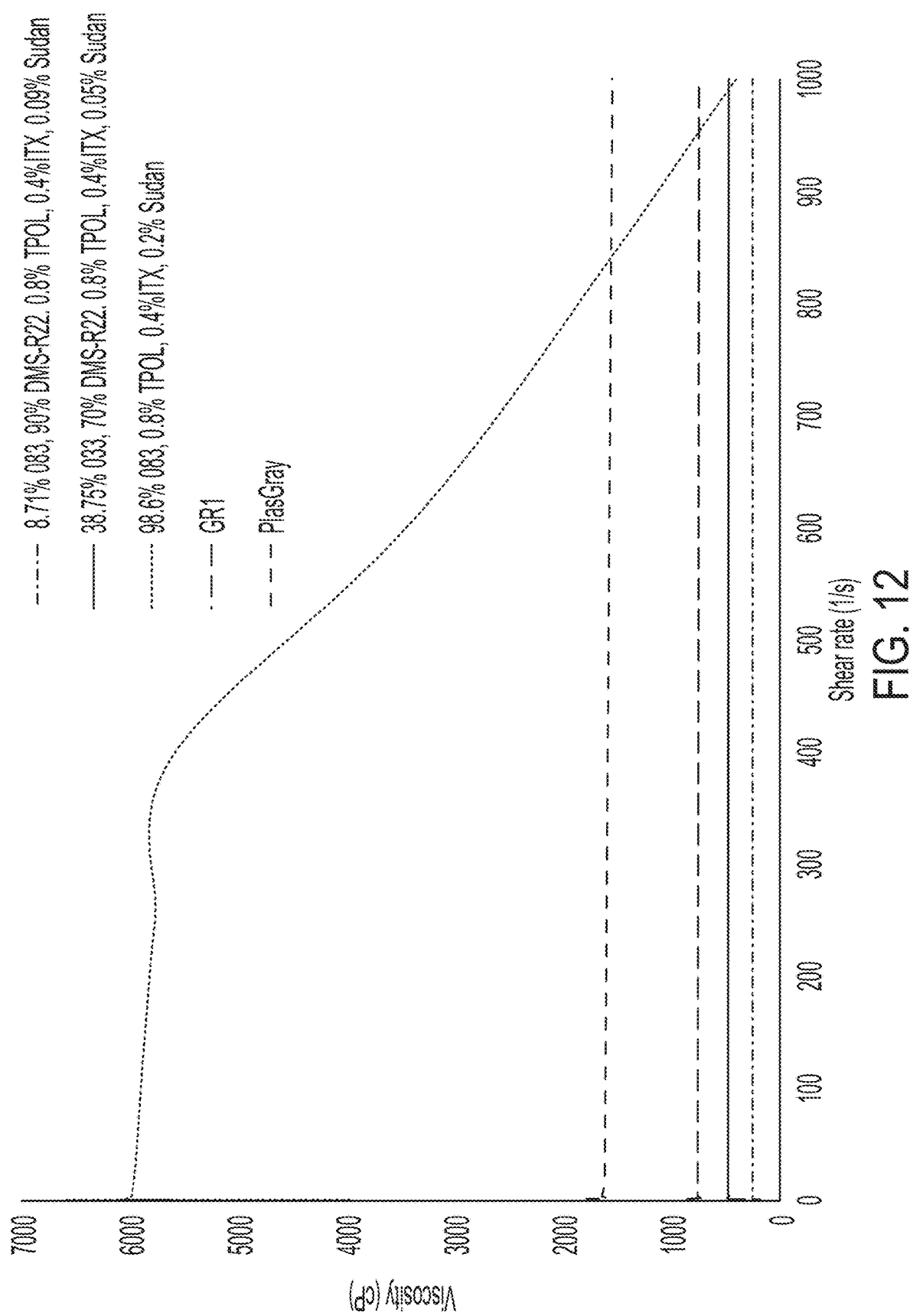
FIG. 12 shows a plot of viscosity (cP) versus shear rate (1/s) for various resin formulations and two commercial resins demonstrating the decrease in viscosity by the combination of RMS-083 (or RMS-033) with DMS-R22. The resin formulations with DMS-R22 result in lower viscosity resins than the commercially available GR1 and PlasGray. The curve without DMS-R22 also demonstrates a pseudoplastic, shear thinning effect.

The printability of 3D printing resins for SLA systems is largely determined by the viscosity of the material. Generally, reducing the viscosity of the resin improves the printability. The resin formulas with only side-chain copolymers (RMS-083 or RMS-033) have a high viscosity, thereby challenging the printability of complex or small features. The end-chain copolymer, DMS-R22, was added to the formula to reduce the overall viscosity of the resin as shown in FIG. 12 and enhance printability.

Figure 13:
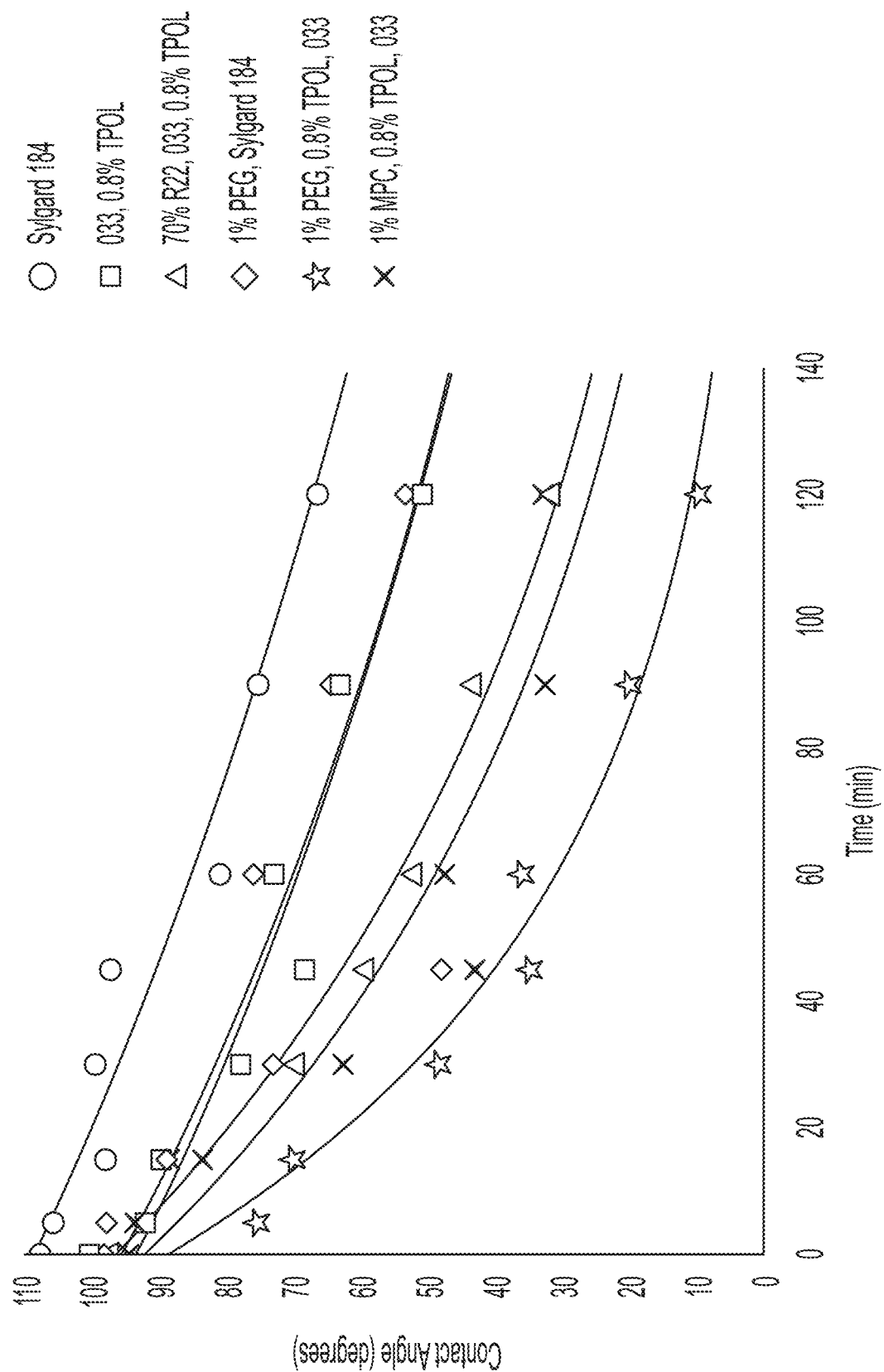
FIG. 13 is a plot of contact angle (degrees) over time (min) for various resin formulations demonstrating the wettability of the cured polymer after the integration of a hydrophobic additive such as a PEG-containing polymer or a zwitterionic molecule. The addition of hydrophilic molecules PEG and MPC decrease contact angle and increase hydrophilicity of the surface. "R22" refers to DMS-R22. "033" refers to RMS-033. The PEG containing hydrophobic additive used for this plot was dimethylsiloxane-(60-70% ethylene oxide) block copolymer, commercially available from Gelest (DBE-712, CAS No. 27306-78-1). The MPC used for this plot was 2-methylacryloyloxyethyl phosphorylcholine (MPC), commercially available from Sigma-Aldrich (CAS No. 67881-98-5).

In the case where the 3D printed part is used with biologic materials, biocompatibility becomes a consideration for material performance. One approach taken to address the possible concerns of biocompatibility is to modify the printed part to create a hydrophilic surface that reduces the adsorption of proteins. Shown in FIG. 13, the incorporation of a zwitterionic compound into the resin formula produces a hydrophilic surface after exposure to water.

It will be apparent to those skilled in the art that various modifications and variations can be made without departing from the scope or spirit of this disclosure. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A photocurable resin comprising:
   a) 5-99% by weight of a copolymer having a methacryloxypropyl-methysiloxane repeating unit represented by formula (I):

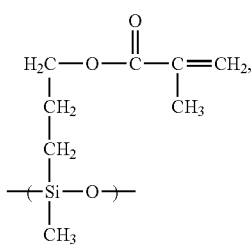

and
a dimethylsiloxane repeating unit represented by formula (II):

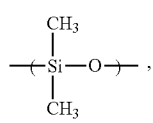

wherein the methacryloxypropyl-methysiloxane repeating unit constitutes 1-10 mol % of the copolymer, and the dimethylsiloxane repeating unit constitutes the balance of the mol % of the copolymer, and
wherein the copolymer has a viscosity average molecular weight ($M_v$) ranging from about 20 kDa to about 60 kDa;
   b) 10-95% by weight of a methacryloxypropyl terminated dimethylsiloxane represented by formula (IV):

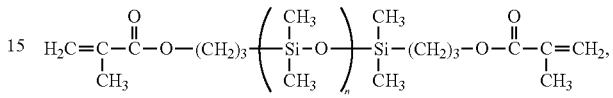

wherein n is an integer ranging from 1 to 350;
   c) 0.01-10% by weight of a phosphine oxide photoinitiator selected from phenylbis (2,4,6-trimethylbenzoyl) phosphine oxide, diphenyl-(2,4,6, trimethylbenzoyl) phosphine oxide (TPO), ethyl (2,4,6-trimethylbenzoyl) phenylphosphinate (TPO-L), or a combination thereof;
   d) 0.01-5% by weight of a photoabsorber selected from 1-Phenyldiazenyl) naphthalen-2-ol (Sudan I) or 1-(2,4-Dimethylphenylazo)-2-naphthol (Sudan II); and
   e) 0.01%-5% by weight of a photosensitizer selected from 2-chloro-thioxanthone, isopropylthioxanthone (ITX), or a combination thereof.

2. The resin of claim 1, further comprising 0.01-20% by weight of a hydrophillic additive, wherein the hydrophillic additive is selected from (i) a polymer or copolymer comprising a poly ($C_1$-$C_4$ alkyl oxide), or (ii) a zwitterion.

3. The resin of claim 2, wherein the hydrophillic additive is selected from a (i) polymer comprising ethylene oxide or (ii) a betaine.

4. The resin of claim 2, wherein the hydrophillic additive is selected from (i) a dimethylsiloxane-(ethylene oxide) block copolymer comprising 60-70 mol % ethylene oxide or (ii) 2-methacryloyloxyethyl phosphorylcholine (MPC).

5. The resin of claim 2, comprising 0.05-2% by weight of the hydrophillic additive.

6. The resin of claim 1, comprising 0.05-10% by weight of TPO-L.

7. The resin of claim 1, comprising 0.5-1% by weight of TPO-L.

8. The resin of claim 1, comprising 0.01-1% by weight of Sudan I.

9. The resin of claim 1, comprising 0.01-0.5% by weight of Sudan I.

10. The resin of claim 1, comprising 0.1-1% by weight of ITX.

11. The resin of claim 1, comprising 0.3-1% by weight of ITX.

12. The resin of claim 1, comprising 5-30% by weight of the copolymer and 50-95% by weight of the methacryloxypropyl terminated dimethylsiloxane.

13. The resin of claim 1, wherein the methacryloxypropyl-methysiloxane repeating unit accounts for 7-9 mol % of the copolymer.

14. A method for stereolithographically printing a 3-D object, comprising:
   a) providing the photocurable resin of claim 1;
   b) selectively photopolymerizing a first portion of the resin to provide a first photocured layer; and c) selectively photopolymerizing a second portion of the resin to provide a second photocured layer, wherein the first and second photocured layers form an integral photocured layer.

15. The method of claim 14, further comprising sequentially repeating steps (b) and (c) until the object is printed.

16. A 3-D microfluidic device printed from the photocurable resin of claim 1.

17. The device of claim 16, wherein the 3-D microfluidic device is an artificial lung.

18. The device of claim 17, wherein the device comprises a first channel for transporting gas and a second channel for transporting blood.

\* \* \* \* \*